(12) United States Patent
Harper et al.

(10) Patent No.: US 7,214,346 B2
(45) Date of Patent: May 8, 2007

(54) OPTOELECTRONIC DETECTION SYSTEM

(75) Inventors: James Douglas Harper, Boston, MA (US); Richard Hart Mathews, Chelmsford, MA (US); Bernadette Johnson, Hollis, NH (US); Martha Susan Petrovick, Barre, MA (US); Ann Rundell, West Lafayette, IN (US); Frances Ellen Nargi, Concord, MA (US); Timothy Stephens, Lexington, MA (US); Linda Marie Mendenhall, Acton, MA (US); Mark Alexander Hollis, Concord, MA (US); Albert M. Young, Fishkill, NY (US); Todd H. Rider, Littleton, MA (US); Eric David Schwoebel, Belmont, MA (US); Trina Rae Vian, Groton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/467,242

(22) PCT Filed: Feb. 6, 2002

(86) PCT No.: PCT/US02/03606

§ 371 (c)(1),
(2), (4) Date: Jan. 16, 2004

(87) PCT Pub. No.: WO02/066683

PCT Pub. Date: Aug. 29, 2002

(65) Prior Publication Data

US 2004/0121402 A1    Jun. 24, 2004

Related U.S. Application Data

(60) Provisional application No. 60/266,977, filed on Feb. 7, 2001.

(51) Int. Cl.
*G01N 21/00* (2006.01)
*G01N 21/01* (2006.01)
*G01N 21/62* (2006.01)
*G01N 21/63* (2006.01)
*G01N 21/64* (2006.01)
*G01N 33/52* (2006.01)

(52) U.S. Cl. .............. 422/82.05; 422/55; 422/58; 422/68.1; 422/82.05; 422/82.06; 422/82.07; 422/82.08; 435/7.1; 435/7.2; 435/7.21; 435/287.1; 435/287.2; 435/288.7; 435/808; 436/164; 436/172

(58) Field of Classification Search .............. 435/7.1, 435/7.2–7.21, 69.6, 287.1–287.3, 288.3, 435/288.7; 422/63, 65–67, 68.1, 72, 82.05, 422/82.08
See application file for complete search history.

(56) References Cited

U.S. PATENT DOCUMENTS 4,493,895 A * 1/1985 Colaruotolo et al. ....... 435/262

(Continued)

FOREIGN PATENT DOCUMENTS

EP    0 823 633 A1    2/1998

(Continued)

OTHER PUBLICATIONS

Davis et al., "The induction of T cell unresponsiveness by rapidly modulating CD3", 1989, J Immunol, vol. 142, pp. 1084-1094.*

(Continued)

*Primary Examiner*—Long V. Le
*Assistant Examiner*—Unsu Jung
(74) *Attorney, Agent, or Firm*—Hamilton, Brook, Smith & Reynolds, P.C.

(57) ABSTRACT

The invention relates to optoelectronic systems for detecting one or more target particles. The system includes a reaction chamber, a specimen collector, an optical detector, and a reservoir containing cells, each of the cells having receptors which are present on the surface of each cell and are specific for the target particle to be detected, where binding of the target particle to the receptors directly or indirectly activates a reporter molecule, thereby producing a measurable optical signal.

19 Claims, 23 Drawing Sheets
(5 of 23 Drawing Sheet(s) Filed in Color)

Integrated BAWS/Sensor Concept

U.S. PATENT DOCUMENTS

| | | | |
|---|---|---|---|
| 4,499,052 A * | 2/1985 | Fulwyler | 422/52 |
| 4,946,778 A * | 8/1990 | Ladner et al. | 435/69.6 |
| 5,055,408 A * | 10/1991 | Higo et al. | 436/48 |
| 5,126,276 A | 6/1992 | Fish et al. | |
| 5,139,937 A | 8/1992 | Inouye et al. | |
| 5,223,409 A * | 6/1993 | Ladner et al. | 435/69.7 |
| 5,360,728 A | 11/1994 | Prasher | |
| 5,541,309 A | 7/1996 | Prasher | |
| 5,578,269 A * | 11/1996 | Yaremko et al. | 422/64 |
| 5,698,450 A * | 12/1997 | Ringrose et al. | 436/526 |
| 5,701,012 A | 12/1997 | Ho | |
| 5,714,666 A | 2/1998 | Pritchett et al. | |
| 5,798,441 A | 8/1998 | Cormier et al. | |
| 5,846,708 A | 12/1998 | Hollis et al. | |
| 5,932,795 A | 8/1999 | Koutrakis et al. | |
| 5,985,214 A * | 11/1999 | Stylli et al. | 422/65 |
| 6,087,114 A * | 7/2000 | Rider | 435/7.2 |
| 6,103,479 A * | 8/2000 | Taylor | 435/7.2 |
| 6,228,610 B1 * | 5/2001 | Flor et al. | 435/69.1 |
| 6,239,453 B1 | 5/2001 | Yamada et al. | |
| 6,248,542 B1 | 6/2001 | Rider et al. | |
| 6,672,947 B2 * | 1/2004 | Tsao et al. | 451/57 |
| 6,800,448 B2 * | 10/2004 | Rider et al. | 435/7.2 |
| 6,872,538 B1 | 3/2005 | Dupriez et al. | |
| 2002/0106786 A1 * | 8/2002 | Carvalho et al. | 435/287.3 |

FOREIGN PATENT DOCUMENTS

| | | |
|---|---|---|
| WO | WO 86/07463 A1 | 12/1986 |
| WO | WO 95/23348 A1 | 8/1995 |
| WO | WO 99/30156 A1 | 6/1999 |
| WO | WO 99/58975 A1 | 11/1999 |
| WO | WO 00/02045 A2 | 1/2000 |
| WO | WO 01/36965 A2 | 5/2001 |

OTHER PUBLICATIONS

Parikh et al., "COOH Terminus of membrane IgG is essential for an antigen-specific induction of some but not all early activation events in mature B cells", J Exp Med, vol. 174, pp. 1103-1109.*

Kostov, Y., et al., "All Solid-State GFP Sensor," Biotechnology and Bioengineering, Including: Symposium Biotechnology In Energy Production and Conservation, John Wiley & Sons. NY, vol. 70(4): 473-477 (2000).

Button, D., et al., "Aequorin-expressing Mammalian Cell Lines Used to Report $Ca^{2+}$ Mobilization," Cell Callcium, 14:663-671, 1993.

Chalfie, M., "Green Fluorescent Protein," Photochemistry and Photobiology, 62(4):651-656, 1995.

Mosier, D.E. "Primary In Vitro Antibody Responses by Purified Murine B Lymphocytes in Serum-Free Defined Medium," The Journal of Immunology, 127(4):1490-1493, 1981.

Paddle, B.M. "Biosensors for Chemical and Biological Agents of Defence Interest," Biosensors & Bioelectronics, 11(11):1079-1113, 1996.

Page, D.L., et al., "A Cell-based Immunobiosensor with Engineered Molecular Recognition-Part II: Enzyme Amplification Systems," Biosensors & Bioelectronics, 12(6):457-466, 1997.

Pizziconi, V.B., et al., "A Cell-based Immunobiosensor with Engineered Molecular Recognition-Part I: Design Feasibility," Biosensors & Bioelectronics, 12(4):287-299, 1997.

Shimomura, O., et al., "Calcium Binding, Quantum Yield, and Emitting Molecule in Aequorin Bioluminescence," Nature, 227:1356-1357, 1970.

Shimomura, O., et al., "Light-emitting Properties of Recombinant Semi-Synthetic Aequorins and Recombinant Fluorescein-conjugated Aequorin for Measuring Cellular Calcium," Cell Calcium, 14:373-378, 1993.

Wilson, H.A., et al., "Crosslinkage of B Lymphocyte Surface Immunoglobulin by Anti-Ig or Antigen Induces Prolonged Oscillation of Intracellular Ionized Calcium," Journal of Experimental Medicine, 166:601-606, 1987.

Wilson, H.A., et al., "The B Lymphocyte Calcium Response to Anti-Ig Is Diminished by Membrane Immunoglobulin Cross-Linkage to the Fcγ Receptor," The Journal of Immunology, 138(6):1712-1718, 1987.

Baylor, D.A., "Photoreceptor Signals and Vision," Investigative Ophthalmology, 28(1):34-49, 1987.

Kombrink, E. and Somssich, I.E., "Defense Responses of Plants to Pathogens," Advances in Botanical Research, 21:1-34, 1995.

* cited by examiner

FIG. 5

B-Cell Response to Foot-and-Mouth Disease Virus

- Tests done at Plum Island USDA BL-3 Facility

Legend:
- Background
- Clone 8; FMDV
- Clone 12; FMDV
- Clone 31; FMDV
- Mutant FMDV X-axis: Time (sec)
Y-axis: Relative Luminescence Virus introduced (at time 0)

Active Antigen Presentation Increases Signal

Automated Cell-Delivery Concept

FIG. 10

Dose Response For Killed Tularemia

Automated Centrifuge-Module Concept

FIG. 16

Direct-Impaction Agent-Delivery System
for Sensor Cell Identification Sensor

Integrated Dry-Impactor/Sensor Concept

FIG. 22

Effects of Cell Treatments on the Response of YP-specific B-cells to killed Yersenia pestis

FIG. 23

OPTOELECTRONIC DETECTION SYSTEM

CROSS-REFERENCE TO RELATED APPLICATIONS

This application is a national phase under 35 U.S.C. 371 of PCT International Application No. PCT/US02/03606 which has an international filing date of Feb. 6, 2002, which designated the United States of America, and claims benefit of U.S. Application Ser. No. 60/266,977, entitled Optoelectronic Detection System, filed Feb. 7, 2001, which application is hereby incorporated by reference in its entirety.

STATEMENT AS TO FEDERALLY SPONSORED RESEARCH

This invention was made with Government funds from U.S. Air Force contract no. F19628-00-C-0002. The Government has certain rights in the invention.

BACKGROUND OF THE INVENTION

The need for small, fast, and sensitive detectors of biological agents which are able to monitor an environment for extended periods of time is underscored by the proliferation of biological and chemical weapons, the poor man's nuclear weapon. Under battlefield conditions, a useful detector would rapidly alert a soldier when a specific biological or chemical agent is detected so that countermeasures can quickly be implemented.

Such detectors would be useful in non-military applications as well. Rapid detection of antibiotic-resistant bacteria in a patient would help clinicians select a more effective therapeutic regimen. Continuous monitoring of a city's drinking water supply would provide early warning of potential pathogens, giving public works officials more time to manage the potential health risks to the public. In addition, the use of these detectors in meat and poultry inspections would be a significant improvement over the current "poke-and-smell" procedure. In general, such detectors are sorely needed analytical and diagnostic applications within the fields of medicine (e.g., veterinary medicine), agriculture, environmental protection (e.g., to diagnose sick building syndrome), and food processing or regulation All vertebrates acquire a specific immune response to a foreign agent (antigen) in part by generating an immense diversity of antibody molecules. Antibody molecules bind to antigen with high specificity, e.g., they can differentially bind to two closely related strains of bacteria, viruses, protein, nucleic acid, fungus, protozoa, multicellular parasite, or prion, as well as products produced or induced by those particles.

Antibodies are produced by B cells, a crucial component of the immune system. An antigen can activate a B cell by binding to antibodies on its surface, leading to a cascade of intracellular biochemical reactions which causes a calcium ion influx into the cytosol of the B cell.

For a review of antibody structure and function and B cell activation, see Paul, editor, Fundamental Immunology, 3rd ed., Raven Press, New York (1993).

SUMMARY OF THE INVENTION

Devices that exploit antibody diversity for detection of multiple and rare target particles or antigens have been described in U.S. Pat. No. 6,087,114 and now U.S. Pat. 6,248,542 filed Oct. 9, 1998, now pending.

These devices generally include a liquid medium containing sensor cells (e.g., a B-cell or fibroblast) an optical detector, and the liquid medium receiving target particles to be detected. Each of the cells has receptors (e.g., chimeric or single chain antibodies) which are expressed on its surface and are specific for the antigen to be detected. Binding of the antigen to the receptor results in a signaling pathway involving chemical or biochemical changes (e.g., an increase in calcium concentration). The cells also contain emitter molecules (e.g., aequorin or indo-1) in their cytosol which can emit photons in response to the signaling pathway (e.g., increased calcium concentration in the cytosol). The detector can be separated from the medium containing the cells by a covering (e.g., glass) that is transparent to the photons. Such a covering can serve to support the medium, protect a fragile surface of the detector, or be used as a lens. The optical detector, e.g., a charge-coupled device (CCD) is able to detect the photons emitted from the cells in response to the receptor-mediated signaling pathway and indicate to the user that the antigen to be detected is present. Other optical detectors which can be used in the device include photomultiplier tubes, photodiodes, complimentary metal oxide semiconductor (CMOS) imagers, avalanche photodiodes, and image-intensified charge-coupled devices (ICCD) (see for example, those available from Photek Ltd., East Sussex, UK). In some embodiments, the optical detector is able to distinguish individual cells.

The present invention is based, in part, on the discovery that, depending on the size of the target particle to be detected, candidate particles to be tested should be mixed with photon-emitting cells either before or after the cells have been deposited in a reaction chamber (e.g., a centrifuge tube). The sequence of deposition was found to dramatically increase or decrease detection efficiency. When the target particle is a bacterium and thus far smaller than a B cell, depositing and pelleting the candidate particles in a centrifuge tube before the B cells were deposited and pelleted in the tube greatly increased detection efficiency. This arises in part from the differential sedimentation rate of particles (e.g., cells and bacteria) having different sizes. If a mixture of cells and bacteria were centrifuged together, cells would be rapidly pelleted while most of the bacteria would remain in the liquid above the pellet for at least some time. In contrast, a pre-spin at high speed that pellets and concentrates the candidate particles, before the larger emitter cells are driven at low speed into the candidate particles, increases rather than decreases contact between cells and particles. If the target particles (e.g., protozoans) are larger than the B cells, then the sequence can be reversed or simplified to a single spin of the B cells and candidate particles. Since the detection systems described herein are dependent on contact between an emitter cell and a target particle, it is important to achieve contact as soon and as efficiently as possible. Therefore, the sequence of localization in a reaction chamber is important for improving detection.

In addition, the de-coupling of the introduction of emitter cells and the introduction of candidate particles into one or more reaction chambers provides system flexibility and allows detection of multiple target particles in multiple samples. For example, multiple emitter cells, each specific for a different target, can be contacted with a single particle sample. Alternatively, identical emitter cells can be contacted with different particle samples. Whether the emitter cells specific for different antigens or target particles are spatially separated in different reaction chambers depends on whether the photon wavelength of different emitter cells is different or the same. If the wavelengths are the same, then the reactions can be, but are not required to be, separated. See U.S. Pat. No. 6,087,114 and now U.S. Pat. No. 6,248,542 for considerations regarding multiplex detection.

In one aspect the invention is an optoelectronic system for detecting a target particle, the system comprising
  a first reaction chamber;
  a specimen collector for collecting candidate particles present in a medium, the collector configured to deposit the candidate particles in the first reaction chamber;
  a first reservoir containing first emitter cells, each of first emitter cells having first receptors (e.g., antibodies) which are expressed on the surface of each first cell and are specific for a first target particle to be detected, wherein each first emitter cell further having a first emitter molecule which, in response to the binding of the first target particle to the first receptors, emits a first photon, wherein the first reservoir is configured to deposit at least a portion of the first cells into the first reaction chamber; and an optical detector arranged for receiving the photon emitted from the cell. The system can further include a rotor adapted to couple the first reaction chamber and, during rotation, apply a centripetal or centrifugal force to the first reaction chamber that is sufficient to collect a substantial portion of the candidate particles or a substantial portion of the first emitter cells in a portion of the first reaction chamber.

In other aspects, the invention is any system herein: wherein the first reaction chamber is mounted on a movable stage, wherein at a first station the stage positions the first reaction chamber in a first configuration that allows the collector to deposit the candidate particles in the first reaction chamber, and wherein at a second station the stage positions the first reaction chamber in a second configuration that allows the first reservoir to deposit at least a portion of the first emitter cells in the first chamber; wherein the optical detector comprises a charge-coupled device, avalanche photodiode, CMOS imager, photomultiplier tube, or other photodetector, or arrays of such detectors; wherein the medium is a gas; wherein the medium is a liquid; wherein the emitter cells are B cells; wherein the B cells have an artificial expression plasmid that encodes the first receptors; wherein the first receptors are single chain antibodies; wherein the first target particle is a virus, bacterium, protein, nucleic acid, fungus, protozoa, multicellular parasite, or prion, as well as products produced or induced by those particles; wherein the first target particle is selected from the group consisting of Foot and Mouth Disease Virus, *Yersinia pestis*, *Francisella tularensis*, and Venezuelan Equine Encephalitis Virus, Brucella spp., Vibrio Cholera, and orthopox viruses (including Smallpox); wherein a portion of the first reaction chamber is coated with a carrier protein; wherein the carrier protein is bovine serum albumin; wherein a portion of the first reaction chamber is coated with poly-L-lysine; further having a control mechanism that deposits the candidate particles and at least a portion of the first cells in sequential order; wherein the sequential order is deposition of at least a portion of the first cells first, and deposition of the candidate particles thereafter; wherein the sequential order is deposition of the candidate particles first, and deposition of at least a portion of the first cells thereafter.

In other aspects, the systems are those herein: further comprising a particle size detector coupled to the control mechanism, the particle size detector arranged to detect the size of candidate particles entering or present in the collector, wherein (1) if the particle size detector detects candidate particles having a size greater than a reference size, then the control mechanism is configured to deposit at least a portion of the first cells first, and deposit the candidate particles thereafter, and (2) if the particle size detector detects candidate particles having a size less than a reference size, then the control mechanism is configured to deposit the candidate particles first, and deposit at least a portion of the first cells thereafter; wherein the control mechanism comprises a movable stage on which the first reaction chamber is mounted, wherein at a first station the stage positions the first reaction chamber in a first configuration that allows the collector to deposit the candidate particles in the first reaction chamber, and wherein at a second station the stage positions the first reaction chamber in a second configuration that allows the first reservoir to deposit at least a portion of the first cells in the first reaction chamber; wherein the first reaction chamber comprises an adhesive surface, and the collector directs a gas stream against the adhesive surface; wherein the first reaction chamber comprises a filter, and the collector forces flow of the medium through the filter; wherein the first reservoir further contains second cells, each of second cells having second receptors (e.g., antibodies) which are expressed on the surface of each second cell and are specific for a second target particle to be detected, wherein each second cell further having a second emitter molecule which, in response to the bindings of the second target particle to the second receptors, emits a second photon, wherein the first reservoir is configured to deposit at least a portion of the second cells into the first reaction chamber, and wherein the second photon has a wavelength different from the first photon.

The systems are also those herein: further comprising a second reservoir containing second cells, each of second cells having second receptors (such as antibodies) which are expressed on the surface of each second cell and are specific for a second target particle to be detected, wherein each second cell further having a second emitter molecule which, in response to the binding of the second target particle to the second receptors, emits a second photon, wherein the first reservoir is configured to deposit at least a portion of the second cells into the first reaction chamber, and wherein the second photon has a wavelength different from the first photon; further comprising a second reaction chamber and a second reservoir containing second cells, each of second cells having second receptors (e.g., antibodies) which are expressed on the surface of each second cell and are specific for a second target particle to be detected, wherein each second cell further having a second emitter molecule which, in response to the binding of the second target particle to the second receptors, emits a second photon, wherein the second reservoir is configured to deposit at least a portion of the second cells into the second reaction chamber, and wherein the candidate particles are also deposited in the second reaction chamber; further comprising an air sampling device; further comprising a biological aerosol warning sensor; and those wherein the air sampling device is an air impactor.

Another aspect of the invention is a method for detecting a target particle in a liquid sample comprising:
a. Adding the liquid sample to a chamber;
b. Adding emitting cells, comprising one or more receptors (e.g., antibodies) suitable for interaction with a target particle and emitter molecules that emit photons (e.g., by luminescence or fluorescence) in response to one or more receptors interacting with the target particle, to the chamber to form a mixture;
c. Measuring for photon emission from the cells in the mixture (e.g., by luminescence or fluorescence).

Another aspect of the invention is a method for detecting a target particle in a liquid sample comprising:
a. Adding the liquid sample to a chamber;
b. Localizing the target particles within the chamber (e.g., by centrifugation, filtration, electrophoresis, dielectrophoresis, magnetic forces (using affinity-capture magnetic beads), acoustics/ultrasonics, or other means);
c. Adding emitting cells, comprising one or more receptors (e.g., antibodies) suitable for interaction with a target particle and emitter molecules that emit photons (e.g., by luminescence or fluorescence) in response to one or more receptors interacting with the target particle, to form a mixture;
d. Localizing the emitter cells within a chamber (e.g., by centrifugation, dielectrophoresis, sedimentation by gravity, or other means to create a high concentration of cells in the same locale as the particles);
e. Measuring for photon emission from the cells in the mixture (e.g., luminescence or fluorescence).

Another aspect of the invention is a method for detecting a target particle in a liquid sample comprising:
a. Adding emitter cells, comprising one or more receptors (e.g., antibodies) suitable for interaction with a target particle and emitter molecules that emit photons (e.g., by luminescence or fluorescence) in response to one or more receptors interacting with the target particle, to a chamber;
b. Localizing the cells within the chamber (e.g., by sedimentation onto a suitable surface to which they will adhere);
c. Adding target particles in a liquid sample to form a mixture;
d. Localizing the target particles (e.g., by allowing sedimentation by gravity, electrophoresis, or other means to create a high concentration of particles in the same locale as the cells);
e. Measuring for photon emission from the cells in the mixture (e.g., by luminescence or fluorescence).

Another aspect of the invention is a method for detecting a target particle in a liquid sample comprising:
a. Adding emitter cells, comprising one or more receptors (e.g., antibodies) suitable for interaction with a target particle and emitter molecules that emit photons (e.g., luminescence or fluorescence) in response to one or more receptors interacting with the target particle, to a chamber;
b. Localizing the cells within the chamber (e.g., by sedimentation onto a suitable surface to which they will adhere);
c. Adding target particles in a liquid sample to form a mixture;
d. Localizing the target particles (e.g., using magnetic-bead capture, filtration (with or without affinity-bead capture), electrophoresis, dielectrophoresis, acoustic/ultrasonic, or other means to concentrate the particles into some locale near the cells);
e. Applying a driving force to the particles (e.g., electrophoresis, magnetism, or other means) or removing the localizing force (e.g., allowing sedimentation by gravity) to bring the concentrated particles into the same locale as the cells;
f. Measuring for photon emission from the cells in the mixture (e.g., by luminescence or fluorescence).

Another aspect of the invention is a method for detecting a target particle in a liquid sample comprising:
a. Adding emitter cells, comprising one or more receptors (e.g., antibodies) suitable for interaction with a target particle and emitter molecules that emit photons (e.g., by luminescence or fluorescence) in response to one or more receptors interacting with the target particle, to a chamber;
b. Localizing the cells within the chamber onto a barrier, permeable membrane, or filter by sedimentation or flow;
c. Adding target particles in a liquid sample to form a mixture;
d. Flowing the sample from the cell side through the barrier, permeable membrane, or filter to allow particle contact with the cells;
e. Measuring for photon emission from the cells in the mixture (e.g., by luminescence or fluorescence).

Another aspect is a method for detecting a target particle in a liquid sample comprising:
a. Adding emitter cells, comprising one or more receptors (e.g., antibodies) suitable for interaction with a target particle and emitter molecules that emit photons (e.g., by luminescence or fluorescence) in response to one or more receptors interacting with the target particle, to a first chamber;
b. Localizing the cells within the first chamber onto a barrier, permeable membrane, or filter by sedimentation or flow;
c. Adding target particles in a liquid sample to a second chamber which connects to the first chamber on the side of the barrier, permeable membrane, or filter opposite the emitter cells;
d. Flowing the sample through the barrier, permeable membrane, or filter under the force of gravity or centrifugation to allow particle contact with the cells;
e. Measuring for photon emission from the cells in the mixture (e.g., by luminescence or fluorescence).

Another aspect of the invention is a method for detecting a target particle in a liquid sample comprising:
a. Adding the liquid sample to a first chamber;
b. Adding emitting cells, comprising one or more receptors (e.g., antibodies) suitable for interaction with a target particle and emitter molecules that emit photons (e.g., by luminescence or fluorescence) in response to one or more receptors interacting with the target particle, to a second chamber, isolated from the first by a controllable membrane (e.g., an electrically-controlled dissolvable gold membrane);
c. Localizing the target particles within the first chamber (e.g., by centrifugation or other means);
d. Causing the membrane to dissolve;
e. Localizing the emitter cells within the first chamber (e.g., by centrifugation, sedimentation by gravity, or other means to create a high concentration of cells in the same locale as the particles);
f. Measuring for photon emission from the cells in the mixture (e.g., by luminescence or fluorescence).

Another aspect of the invention is a method for detecting a target particle in an air sample comprising:
a. Localizing target particles from the air sample by impacting, electrostatic attraction, or settling from still air onto a surface or the interior surface of a chamber;
b. Adding emitting cells, comprising one or more receptors (e.g., antibodies) suitable for interaction with a target particle and emitter molecules that emit photons (e.g., by luminescence or fluorescence) in response to one or more receptors interacting with the target particle, to form a mixture;
c. (optionally) Localizing the emitter cells in the mixture (e.g., by fluid removal by filtration or wicking, centrifugation, dielectrophoresis, sedimentation by gravity, or other means to create a high concentration of cells in the same locale as the particles);

d. Measuring for photon emission from the cells in the mixture (e.g., by luminescence or fluorescence).

In other aspects, the methods are any herein: wherein the sample is air or liquid; wherein emitting cells are B-cells; wherein the emitting cells include antibodies to the target particle; wherein the emitting cells comprise expression plasmids that encode the antibodies; wherein the emitting cells comprise nucleic acids that encode for aequorin; wherein the emitting cells comprise fibroblasts suitable for inducing calcium mobilization; wherein the measuring includes using a photomultiplier tube, photomultiplier array tube, or array of photomultiplier tubes; wherein the measuring includes using a charge-coupled device, a avalanche photodiode or array of avalanche photodiodes, a CMOS imager, or an image-intensified charged-coupled device (ICCD).

In other aspects, the methods are any herein: wherein the application of centrifugal force and measuring for photon emission is performed in a single apparatus and with the sample mixture in a single sample receptacle; wherein the application of centrifugal force and the measuring for photon emission is performed in 30 seconds or less (e.g., 10 seconds or less, 5 seconds or less); wherein the entire method is performed in 10 minutes or less (e.g., 5 minutes or less, 2 minutes or less, 1 minute or less); wherein a sample is simultaneously analyzed for a plurality of target particles; wherein a plurality of samples are simultaneously analyzed for a target particle; wherein a plurality of samples are simultaneously analyzed for a plurality of target particles; wherein 1–20 (e.g., 1–10) samples are simultaneously analyzed for 1–100 (e.g., 1–5.0, 1–25) target particles; wherein the emitter molecule is in the cytoplasm; wherein the samples are simultaneously analyzed for target particles in a single device; wherein the samples are simultaneously analyzed for target particles in a single device having 1 to 10 channels; wherein the target particle is Foot and Mouth Disease virus (FMDV), Venezuelan Equine Encephalitis (VEE) virus, *Yersinia pestis, Francisella tularensis*, Brucella spp., the O1 and O139 strains of *Vibrio cholera*, or orthopox viruses; and wherein a system herein is used.

The systems are also those herein: further comprising 1 to 10 channels; wherein a sample is simultaneously analyzed for a plurality of target particles; wherein a plurality of samples are simultaneously analyzed for a target particle; wherein a plurality of samples are simultaneously analyzed for a plurality of target particles; having dimensions of 12 inches×12 inches×12 inches or less (e.g., 6 inches×4 inches×1 inch or less).

The systems of the invention are useful in analytical and diagnostic applications within the fields of medicine (e.g., veterinary medicine), agriculture, environmental protection (e.g., to diagnose sick building syndrome), and food processing or regulation.

Other features or advantages of the present invention will be apparent from the following detailed description, and also from the claims.

DESCRIPTION OF DRAWINGS

The patent or application file contains at least one drawing executed in color. Copies of this patent or patent application publication with color drawings will be provided by the Office upon request and payment of the necessary fee.

FIG. 5 illustrates the B-cell response to foot-and-mouth disease virus in the optoelectronic sensor.

FIG. 10 illustrates a dose response relationship for a sample of tularemia cells using the optoelectronic sensor.

FIG. 16 is a schematic illustrating an air impactor/optoelectronic sensor

FIG. 22 illustrates the effect of cell treatments on the response of *Yersenia pestis* specific B-cells.

FIG. 23 illustrates an impactor configured to collect aerosol samples.

DETAILED DESCRIPTION

Figure 1:
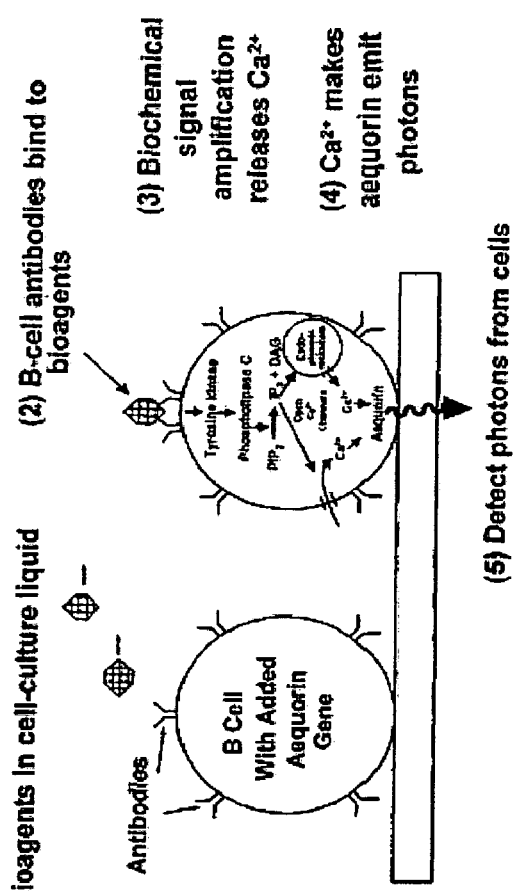
FIG. 1 is a schematic of the optoelectronic sensor cellular concept.
Figure 2:
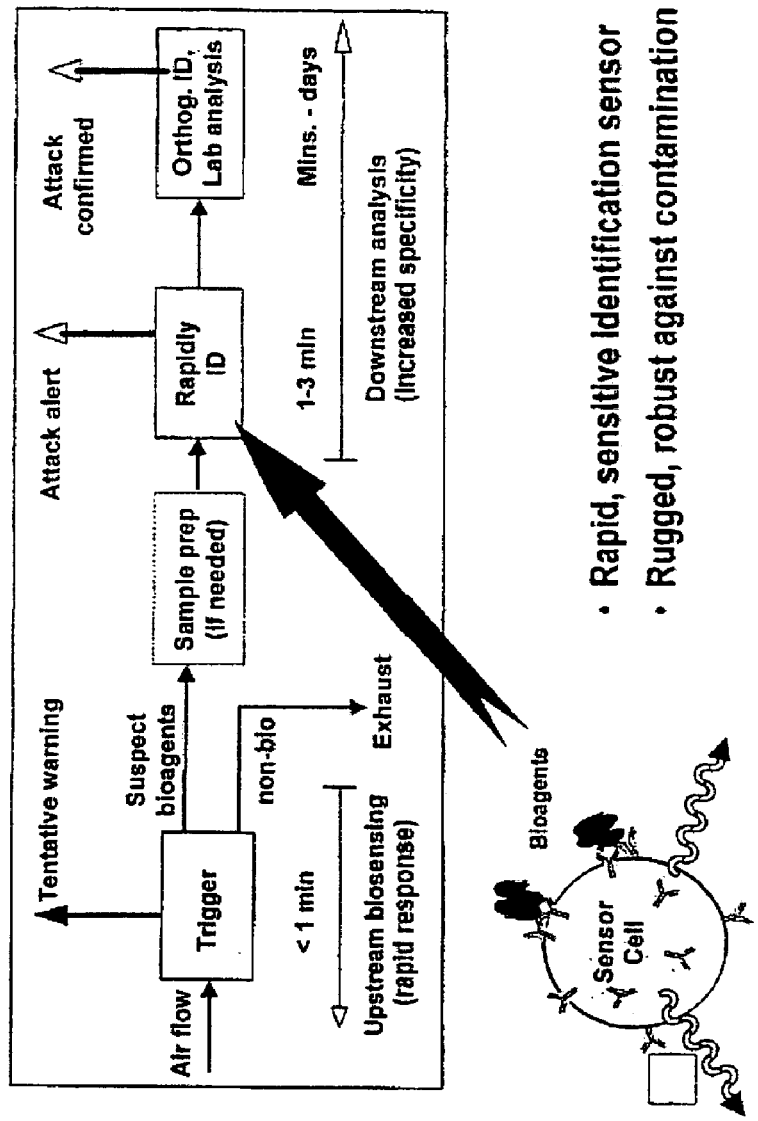
FIG. 2 is a schematic showing the general architecture of an optoelectronic sensor having a sampler (trigger) for preliminary sensing of suspect agents.
Figure 3:
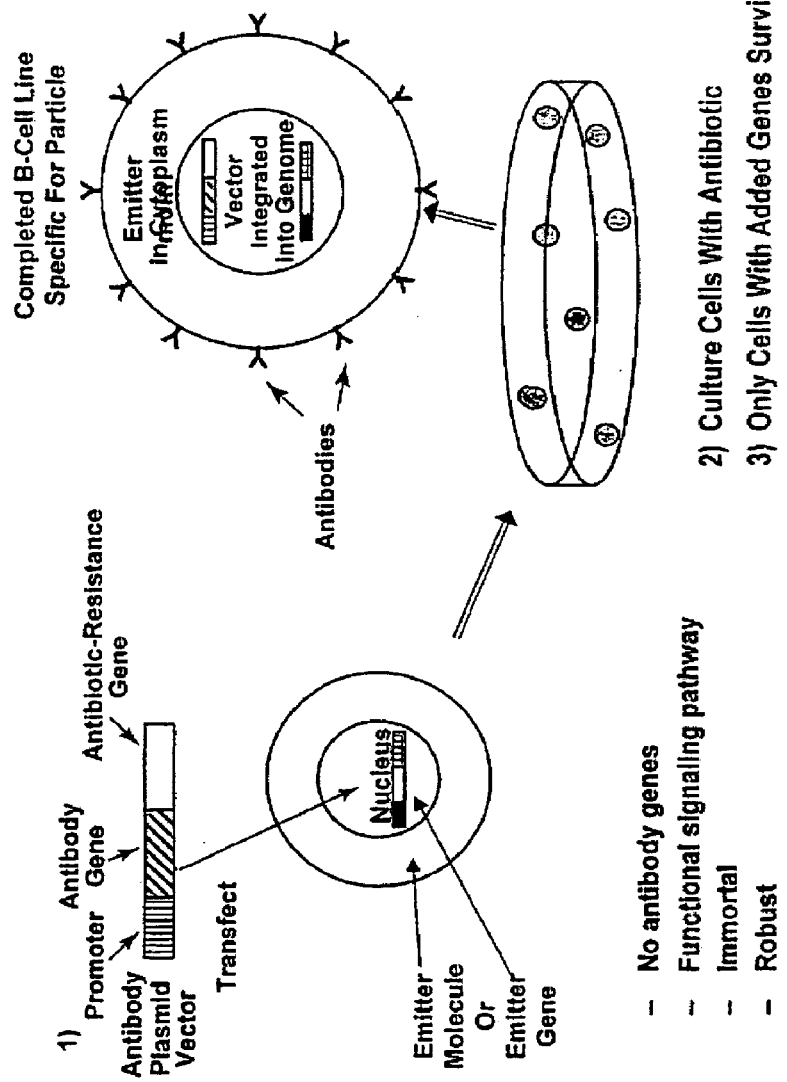
FIG. 3 is a schematic illustrating the creation of cell lines for use in the optoelectronic sensor.

The invention relates to detection systems based on cells having antibodies on their surface and containing a compound that emits a photon upon external stimulation by an antigen or target particle. The materials and procedures suitable for use in the invention are described below.

Cells

The cell could be any prokaryotic or eukaryotic cell that has a suitable receptor, signaling pathway, and signal output method, either naturally, through genetic engineering, or through chemical addition. The cell could even be an artificial or nonliving unit provided that it has a functional receptor, signaling pathway, and signal output method. Upon binding of antigen to the antibodies, the cell mobilizes calcium ions into the cytosol. An example of a cell useful in the device and methods of the invention is a B cell (i.e., a B cell from a cold or warm-blooded vertebrate having a bony jaw) which can be genetically engineered to express one or more surface-bound monoclonal antibodies. The monoclonal antibody can be produced by, for example, immunizing an animal with the antigen to be detected and harvesting the B cell from the immunized animal. DNA encoding the monoclonal antibody can then be isolated and transferred into an immortalized cell line and the cells screened for production of a surface monoclonal antibody specific for the antigen to be detected. B-cells are useful for both qualitative and quantitative analyses, particularly because the emission signal from them typically does not significantly diminish as additional target specimen is exposed to it and also because such emission signal is linear.

Alternatively, the cell can be a fibroblast. However, fibroblasts do not contain the signal transduction machinery necessary to transfer a signal from the cytoplasmic portion of a surface antibody to calcium stores in the cell. To overcome this problem, a chimeric surface antibody can be expressed in the fibroblast. This chimeric antibody contains a cytoplasmic amino acid sequence derived from a polypeptide (e.g., a fibroblast growth factor receptor) that can transduce a signal from the inner surface of the plasma membrane of the fibroblast to intracellular calcium stores. Thus, when an antigen binds to the extracellular portion of the chimeric antibody to cause antibody aggregation on the surface, calcium mobilization is induced. A similar strategy using chimeric antibodies can be employed for any other cell type which is not a B cell, so that the cell is suitable for use in the devices and methods of the invention.

Cells useful in the devices and methods herein are those designed to recognize a specific substance, including those having receptors on their surface that specifically bind to that substance. A preferred receptor is an antibody or single-chain antibody, although other suitable receptors include a mitogen receptor (such as a lipopolysaccharide (LPS) receptor), a macrophage scavenger receptor, a T cell receptor, a cell adhesion molecule, a DNA binding protein such as part of a sequence-specific restriction enzyme or transcription factor, single-stranded-RNA- or double-stranded-RNA-binding protein, an oligonucleotide complementary to a DNA or RNA sequence to be recognized, or other ligand-binding receptor (e.g., Fas; cytokine, interleukin, or hormone receptors; neurotransmitter receptors; odorant receptors; chemoattractant receptors, etc.) that will specifically bind the substance to be recognized. The receptor can be attached to the cell surface via a transmembrane domain, a membrane-bound molecule that specifically binds to the receptor (such as Fc receptors bind to antibodies), or a covalent or noncovalent attachment (e.g., biotin-streptavidin, disulfide bonds, etc.) to a membrane-bound molecule. The receptor can also be a chimeric molecule; for instance, it can have an extracellular domain such as an antibody, single-chain antibody, lectin or other substance-specific binding domain or peptide, and an intracellular domain such as that from the insulin receptor, fibroblast growth factor, other protein that triggers a second messenger cascade, etc. Instead of directly binding to the substance to be recognized, the receptor might specifically bind to another molecule or object that in turn specifically binds to the substance to be recognized, such as a secondary antibody, labelled bead, antigen-conjugated oligonucleotide, etc.

Alternatively, only one of these binding steps may need to be specific. For instance, DNA or RNA containing specific sequences may be pulled out of solution using oligonucleotide probes conjugated to one antigen (or directly to a bead, or on a matrix), and a second set of nonspecific antigen-conjugated oligonucleotide probes annealed to the target DNA/RNA would be used to stimulate cells specific for that second antigen. Also, non-specific nucleic acid binding proteins (histones, protamines, RNA-binding proteins) expressed as chimeras on the cell surface, or antibodies against those binding proteins, could also be used to detect the presence of nucleic acids after a sequence specific selection step.

Antibodies

Whatever original cell type, the antigen-binding variable regions of monoclonal antibodies can obtained either as DNA sequence from a public source, or cloned by RT-PCR from a hybridoma cell line. RT-PCR is accomplished using sets of primers designed to anneal, at the 5-prime end, to either the leader or framework regions of the variable region, and at the 3-prime end to the constant region.

The antibody variable regions are then cloned into expression vectors that already contain the constant regions for light and heavy chain. The light chain expression vector described in Bradbury, Gene 187:9–18, 1997 is especially suitable for this purpose. VKExpress, described in Bradbury, contains the EF-1α promoter, a leader sequence, multiple cloning sites, and the human Ig kappa constant region and polyadenylation signal. The heavy chain expression vector is derived from Invitrogen's pDisplay. This vector contains a CMV promoter, a leader sequence, an HA tag, multiple cloning site, and myc tag, followed by the PDGFR transmembrane domain and bovine growth hormone polyadenylation signal.

pDisplay can be modified for heavy chain expression as follows. The PDGFR transmembrane domain of pDisplay is replaced with the murine IgM constant region without the exon that allows for secretion. This ensures that the protein will remain membrane-bound. The neomycin-resistance gene can be replaced by any of a number of antibiotic-resistance genes including, but not limited to, hygromycin, bleomycin, puromycin, kanamycin, and blasticidin genes. The heavy chain (or alternatively light chain) variable region can be inserted in a two-step process, using overlap-extension PCR, to remove the HA and myc tags present on either side of the multiple cloning site of pDisplay. A vector can also be developed to allow insertion of an overlap extension product containing the variable region fused to approximately 300 base pairs of the IgM constant region, so that cloning can be done in a single step.

The examples below were implemented using the antibody vector construction procedure described immediately above.

An antibody which specifically binds to the antigen to be detected is a molecule which binds to the antigen or an epitope of the antigen, but does not substantially bind other antigens or epitopes in the sample. Such antibodies can be chimeric (i.e., contain non-antibody amino acid sequences) or single chain (i.e., the complementarity determining region of the antibody is formed by one continuous polypeptide sequence).

Alternatively, surface antibody-producing cells can be obtained from the animal and used to prepare a monoclonal population of cells producing surface antibodies by standard techniques, such as the hybridoma technique originally described by Kohler et al., Nature 256:495–497 (1975); Kozbor et al., Immunol Today 4:72 (1983); or Cole et al., Monoclonal Antibodies and Cancer Therapy, Alan R. Liss Inc., pp. 77–96 (1985). The technology for producing cells expressing monoclonal antibodies is well known (see, e.g., Current Protocols in Immunology (1994) Coligan et al. (eds.) John Wiley & Sons, Inc., New York, N.Y.), with modifications necessary to select for surface antibodies rather than secreted antibodies.

Any of the many well known protocols used for fusing lymphocytes and immortalized cell lines can be applied for the purpose of generating a cell producing a surface monoclonal antibody (see, e.g., Current Protocols in Immunology, supra; Galfre et al., Nature 266:55052, 1977; Kenneth, In Monoclonal Antibodies: A New Dimension In Biological Analyses, Plenum Publishing Corp., New York, N.Y., 1980; and Lerner, Yale J Biol Med 54:387–402 (1981). Moreover, the ordinarily skilled worker will appreciate that there are many variations of such methods which also would be useful.

Polyclonal cells expressing antibodies can be prepared by immunizing a suitable animal with the antigen to be detected. The cells producing antibody molecules directed against the antigen can be isolated from the animal (e.g., from the blood) and further purified by well-known techniques, such as panning against an antigen-coated petri dish. As an alternative to preparing monoclonal cells, a nucleic acid encoding a monoclonal antibody can be identified and isolated by screening a recombinant combinatorial immunoglobulin library (e.g., an antibody phage display library) with the antigen to thereby isolate immunoglobulin library members that bind the antigen. Kits for generating and screening phage display libraries are commercially available (e.g., the Pharmacia Recombinant Phage Antibody System, Catalog No. 27-9400-01. Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al., Bio/Technology 9:1370–1372 (1991); Hay et al., Hum Antibod Hybridomas 3:81–85 (1992); Huse et al., Science 246:1275–1281 (1989); Griffiths et al., EMBO J 12:725–734 (1993).

After the desired member of the library is identified, the specific sequence can be cloned into any suitable nucleic acid expressor and transfected into a cell such as a fibroblast. The expressor can also encode amino acids operably linked to the antibody sequence as appropriate for the cell which is to express the antibody. As discussed above, the cytoplasmic transmembrane sequence of a fibroblast growth factor receptor can be linked to a single-chain antibody specific for the antigen to be detected, so that the cell immobilizes calcium when contacted with the antigen. Although separate recombinant heavy chains and light chains can be expressed in the fibroblasts to form the chimeric antibody, single chain antibodies also are suitable (see, e.g., Bird et al., Trends Biotechnol 9:132–137, 1991; and Huston et al., Int Rev Immunol 10:195–217, 1993).

Photon Emitter Molecules

Binding of the desired substance to the cell-surface receptor should trigger a signaling pathway inside the cell. A preferred signaling pathway is the second-messenger cascade found in B cells, T cells, mast cells, macrophages, and other immune cells, wherein crosslinking of the cell surface receptors activates a tyrosine kinase, which then phosphorylates phospholipase C, which then cleaves phosphatidylinositol 4,5-bisphosphate (PIP2) into inositol 1,4,5-trisphosphate (IP3) and diacylglycerol; IP3 then opens calcium channels to release calcium from intracellular stores such as the endoplasmic reticulum or to let in extracellular calcium, thereby elevating the calcium concentration in the cell's cytosol. Depending on the receptor type, cell type, and desired signaling method, alternative second-messenger cascades could be employed, such as a G-protein-adenylyl cyclic-cAMP-protein kinase A cascade.

A method should be provided for monitoring the internal signaling of the cell in response to substances to be identified. If the internal signaling involves an increase in cytoplasmic calcium, a preferred detection method is a calcium-sensitive luminescent or fluorescent molecule, such as aequorin, obelin, thalassicolin, mitrocomin (halistaurin), clytin (phialidin), mnemopsin, berovin, Indo-1, Fura-2, Quin-2, Fluo-3, Rhod-2, calcium green, BAPTA, cameleons (A. Miyawaki et al (1999) Proc. Natl. Acad. Sci. 96, 213540), or similar molecules. It is anticipated that the relative intensities of light and the sensor cell storage characteristics enabled by using calcium-sensitive molecules may vary depending on the efficiency of light production for the specific emitter molecule and the half-life of the activated emitter molecule—in some cases providing significant benefits (e.g., improved sensitivity, quantitative or qualitative detection). Additional performance enhancements may arise from the use of structural analogs of the natural cofactors of photoprotein emitter molecules. Various calcium-sensitive fluorescent dyes which can be taken up by live cells are available from commercial sources, including Molecular Probes, Inc., Eugene, Oreg. Proteins such as aequorin, obelin, thalassicolin, mitrocomin (halistaurin), clytin (phialidin), mnemopsin, berovin or cameleons could be added genetically, injected into the cells, or delivered by a protein uptake tag from HIV TAT (approximately amino acids 47–57; A. Ho et al. (2001) Cancer Research 61, 474–477) or by other means. If desired, such reporter molecules can include targeting signals to target them to the cytoplasmic face of the endoplasmic reticulum or the plasma membrane, the interior of the mitochondria, or other locations where the change in local calcium concentration might be particularly large. Optical methods of detecting activity from other points in the signaling pathway could also be used, such as fluorescence resonance energy transfer (FRET) of fluorescent groups attached to components of the signaling pathway (S. R. Adams et al. (1991) Nature 349, 694–697). Where the internal signaling involves an increase in reactive oxygen species (e.g. superoxide anion radicals, hydroxyl radicals, compound I or II of horseradish peroxidaase, etc.), a preferred detection method is a reactive-oxygen-sensitive luminescent or fluorescent molecule, such as the photoprotein pholasin (a 34-kDa glycoprotein from the bioluminescent mollusc, *Pholas dactylus*) or similar molecules. Alternatively, a reporter gene for any luciferase could be linked to a promoter induced by the signaling pathway. In some cells such as T cells and mast cells, the signaling pathway triggers exocytosis of granules containing proteases such as granzymes, tryptases, or chyrnases. Exocytosis of these proteases could be detected by calorimetric or fluorometric methods (e.g., p-nitroanaline or 7-amino-4-trifluoromethyl coumarin (AFC) linked to peptides cleaved by the proteases [S. E. Lavens et al. (1993) J. Immunol. Methods 166, 93; D. Masson et al. (1986) FEBS Letters 208, 84; R&D Systems]). Also, microelectrodes or other methods to detect the electrical activity associated with the calcium flux or other signaling ion fluxes are suitable to monitor signaling response in the cell.

A suitable emitter molecule is any molecule that will emit a photon in response to elevated cytosolic calcium concentrations, including bioluminescent and fluorescent molecules. One emitter molecule, the bioluminescent aequorin protein, is described in Button et al., Cell Calcium 14:663–671 (1993); Shimomura et al., Cell Calcium 14:373–378 (1993); and Shimomura, Nature 227:1356–1357 (1970). Aequorin generates photons by oxidizing coelenterazine, a small chemical molecule. Coelenterazine diffuses through cellular membranes, so coelenterazine or an analog thereof can be added to the culture medium surrounding the cells. Alternatively, genes encoding enzymes that make coelenterazine can be introduced into the cells. In another embodiment, bioluminescent green fluorescent protein (GFP) (see Chalfie, Photochem Photobiol 62:651–656 [1995]) or yellow fluorescent protein (YFP) can be used. In this embodiment, the cell cytosol contains both GFP and aequorin. In response to elevated calcium in the cytosol, aequorin donates energy to GFP in an emissionless energy transfer process. GFP then emits the photon. Alternatively, the emitter molecule can be a calcium-sensitive fluorescent molecule (e.g., indo-1) which is illuminated by a wavelength of light suitable to induce fluorescence.

Aequorin, or any other emitter molecule, can be introduced into the cell by methods well known in the art. If the emitter molecule is a protein (as is the case with aequorin), the cell can contain an expression vector encoding the protein (i.e., a nucleic acid or virus which will produce the emitter molecule when introduced into a cell). An expression vector can exist extrachromosomally or be integrated into the cell genome.

Reaction Chambers

The reaction chambers suitable for use in the invention can be any substrate or vessel to which emitter cells and candidate particles can be mixed and contacted to each other. In one embodiment, the reaction vessel is a centrifuge tube (e.g., a microcentrifuge or Eppendorf tube). As described herein, centrifugation is a particularly well-suited means to pellet candidate particles or emitter cells first, before the other is driven into the first pellet. To further increase the pelleting of both particles and cells, the side walls of the tube can be coated with a non-sticky carrier protein such as bovine serum albumin to prevent the sticking of emitter cells to the side walls, and the bottom of the tube can be coated with poly-L-lysine to help ensure that the target particles stay adhered to the bottom of the tube. Other proteins or molecules that either prevent or promote cell adhesion are known in the art of cell biology and are suitable for use in the invention.

Centrifuge tubes with customized sample well geometries can provide an additional embodiment that uses centrifugation to increase B cell interactions with difficult-to-sediment particles and reduces the need to customize spin sequence. In this embodiment the particle-containing sample to be analyzed is placed in a tube where the maximum width of the sample chamber is approximately equal to the diameter of an emitter cell. Layering a concentrated emitter cell suspension over the sample followed by centrifuging drives a large number of closely packed emitter cells through the smaller particles while the constrained geometry increases the probability of emitter-cell antibody interaction with particles. Binding of the cell-associated antibody to the particle captures the poorly sedimenting particle and will rapidly draw it to the bottom of the tube with the emitter cell where the resulting light can be observed by a photo multiplier device.

In another embodiment, the reaction chambers are wells in a two-dimensional array, e.g., a microtiter plate, or spots or wells along a tape, as shown in the figures. These arrangements allow multiplex detection of either multiple samples and/or multiple target particles. For automated delivery of candidate particles and/or emitter cells, either the reaction chambers or the specimen collector and emitter cell reservoir is addressable in at least two dimensions. The wells of arrays can also be treated with sticky and non-sticky coatings as described above for centrifuge tubes to facilitate contact between emitter cells and candidate particles.

Specimen Collectors

Different devices can be used to collect samples from, e.g., air. In general, an air sampling device has a collection chamber containing liquid through or beside which air or gas is passed through, or containing a porous filter that traps particulates (e.g., target particles) as air or gas passes through the filter. For collection chambers containing liquid, the collection liquid can be centrifuged or otherwise treated to separate particles from the liquid. The separated particles are then deposited in a reaction chamber. For collection chambers containing a filter (e.g., nitrocellulose), the filter or portions of the filter can act as the reaction chamber. Alternatively, particles can be washed from the filter, or the filter can be dissolved or otherwise removed from the particles. A filter collection chamber can also be adapted to collect particles from a liquid (e.g., water supply sample or cerebral spinal fluid) flowing through the filter. In addition, as discussed above, a liquid sample can be centrifuged to remove any particulate material present in the liquid. A variety of samplers are known and available for use with the present invention. See SKC, Inc., which sells the SKC BIOSAMPLER®, a glass bioaerosol collector, and other sampling devices.

Other air samplers can be used. For example, an alternative device is the Air-O-Cell sampling cassette (SKC, Inc.). In this device, the airborne particles are accelerated and made to collide with a tacky slide which is directly suitable for various staining procedures and microscopic examination.

Aerosol particulates may be collected using inertial separation in a device known as an impactor. An airflow containing particles to be collected is drawn from the environment of interest into the impactor where it is directed towards a surface for impaction. With appropriate geometrical parameters and flow rates in the impactor, particles with sufficient inertia will not follow the flow streamlines, but will impact onto the surface. A significant proportion of the particles impacting the surface adhere through electrostatic and/or van der Waals interactions and are thereby collected and concentrated. In this way, aerosol particles containing proteins (including toxins), viruses, bacteria (vegetative and spore forms), parasites, pollen and other detectable substances can be collected for detection using a variety of available assay technologies including the devices and methods herein.

Dry sample collection for bioassays using an air impactor provides general advantages over traditional air-to-liquid sample collection by reducing or eliminating fluid consumables and transfer mechanisms which reduces assay cost and simplifies automation. Of particular benefit to the devices and methods herein, collection using dry impaction ensures that all of the collected sample is located on the surface prior to the addition of sensor cells of the devices and methods herein, regardless of the size of the individual analyte particles. This achieves localization of all analytes regardless of their sedimentation coefficient in fluid, thereby maximizing the sensitivity of the devices and methods herein and accelerating many implementations of the assay by eliminating a time-consuming step.

Any surface that retains a proportion of particles that impact onto it and that is compatible with subsequent bioassays is suitable as a collection surface. Suitable materials include biocompatible metals, plastics, glasses, crystals, aerogels, hydrogels, papers, etc. Particularly useful configurations of these materials include microcentrifuge tubes, multi-well plates used in high-throughput screening, continuous tapes, filters, conjugate release pads of lateral flow immunoassays, etc. The collection efficiency can be increased by modifications to the collection surface including: the addition of coatings promoting adhesion of biological particles (these coatings can be chemical or biochemical in nature, e.g. polylysine), increased surface roughness to increase the surface area available for collection, and customized surface geometries that promote deposition of particles in defined regions on the surface. Furthermore, additional improvements in collection efficiency can be achieved by manipulating the electrostatic charges on the collection surface and the incoming particles such that additional attractive forces are generated.

Additional improvements can be made to the dry impaction collector by using an air-to-air concentrator upstream of the collector to increase the number of particles in each unit of air sample impacted onto the collection surface. This can significantly reduce the amount of time needed to collect a sufficient number of aerosol particles to provide reliable results for the detector.

Figure 23:
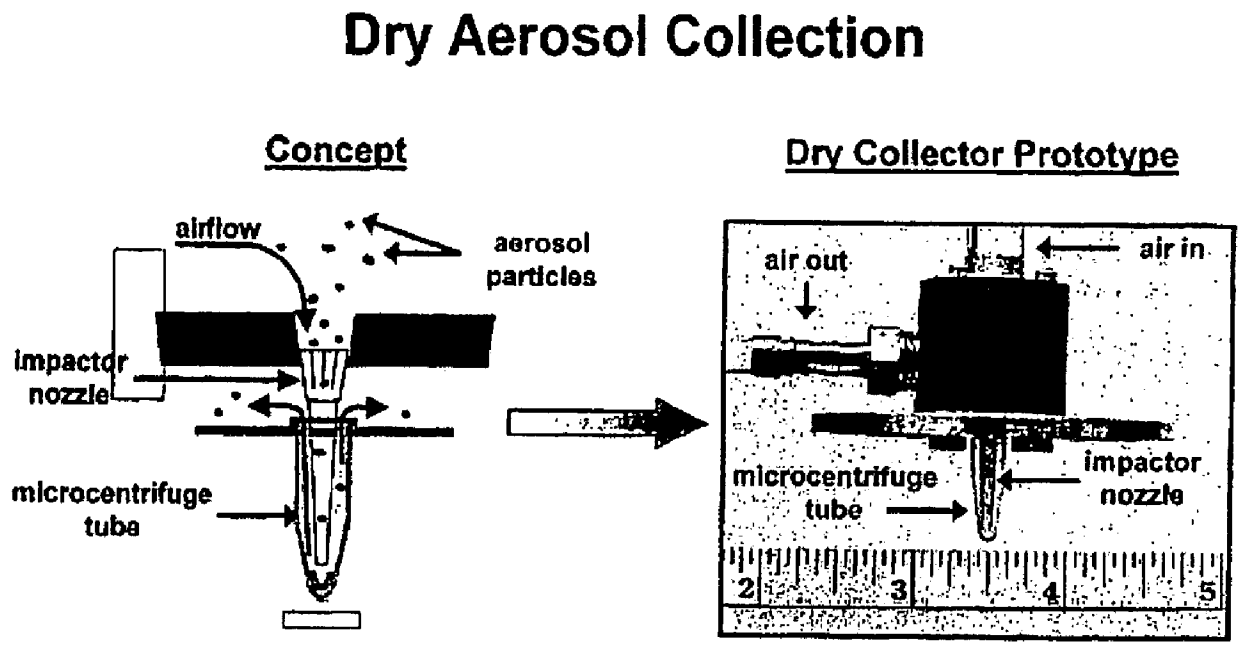

In one example of this collection concept, the impactor described in FIG. 23 has been configured to collect aerosol samples on the bottom of a commercially available plastic tube. A nozzle projects down into the tube and the exit is positioned at the radius of curvature of the tube's inner surface. This positioning increases the likelihood of particle impaction upon the tube bottom where the device sensor cells are most likely to contact them. Once collection is completed, a single droplet containing device sensor cells is added directly to the tube containing collected aerosol particles, spun for 5 seconds to accelerate cell delivery to the tube surface, and emitted light is measured using a photon detector (e.g., PMT, CCD, photodiode, etc.) Using this apparatus, dry bacterial spores can be collected from an aerosol and identified directly with optoelectronic device in less than one minute. This method can be implemented with a plurality of tubes used to collect samples and an automated system to conduct subsequent assays. An example of how a system capable of conducting at least 10 independent assays is shown in FIGS. 4, 6, 9, 12, and 15. By implementing an approach where assays are made capable of looking for multiple analytes in a single tube (multiplexed) the number of detectable substances for a single assay cycle can be made greater than the number of available tubes. This can be done by creating individual optoelectronic detection device cell lines expressing a plurality of receptors with affinity for different analytes or by combining multiple cell lines with different specificities in a single tube.

Figure 4:
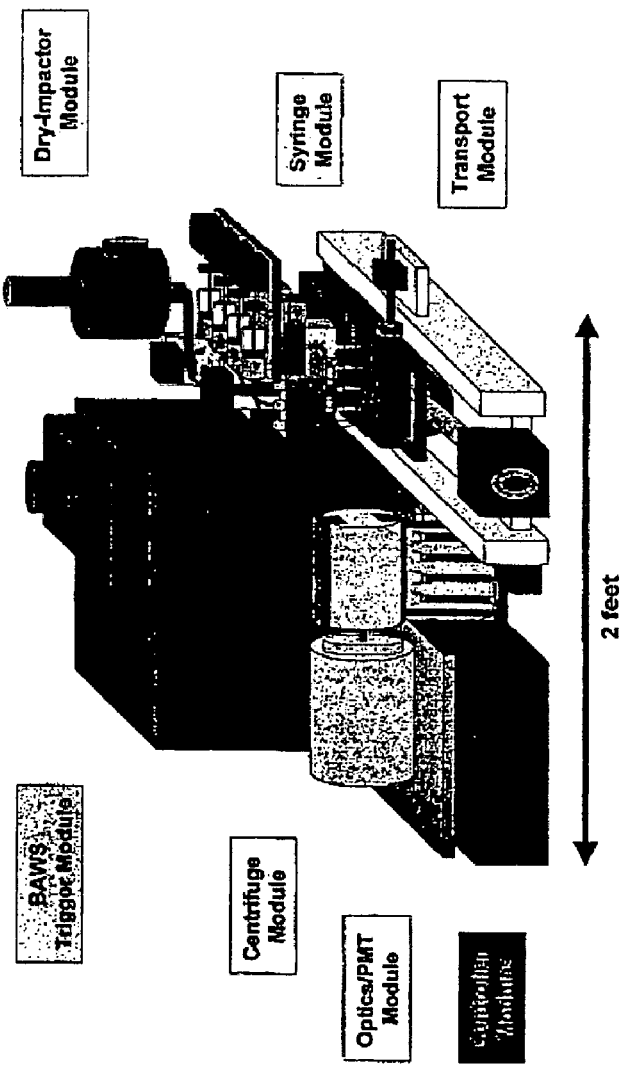
FIG. 4 is a schematic of an integrated biological aerosol warning sensor (BAWS)/optoelectronic sensor system.

FIG. 4 is a schematic of an integrated biological aerosol warning sensor (BAWS)/optoelectronic sensor system. The BAWS trigger module is used to preliminarily detect the presence of particles, e.g., those of a pre-determined size range. If particles meeting specifications are detected, BAWS triggers an air-to-air concentrator that allows particles of a particular size range to be collected and deposited in a well (e.g., reaction chamber, tube) via a dry-impactor module. The dry-impactor module allows for dry sample collection and is in communication with a syringe module for cell (e.g., emitting cells) delivery into a reaction chamber (e.g., tube). A transport module is used to transfer the reaction chamber assembly (having one or more chambers or tubes) to a centrifuge module for sedimentation or mixing of the particle sample and cells. The centrifuge module can be, but need not necessarily be, in communication with an optics/PMT module for detection of photon emission. A controller module is useful for control of operation of the system.

Figure 6:
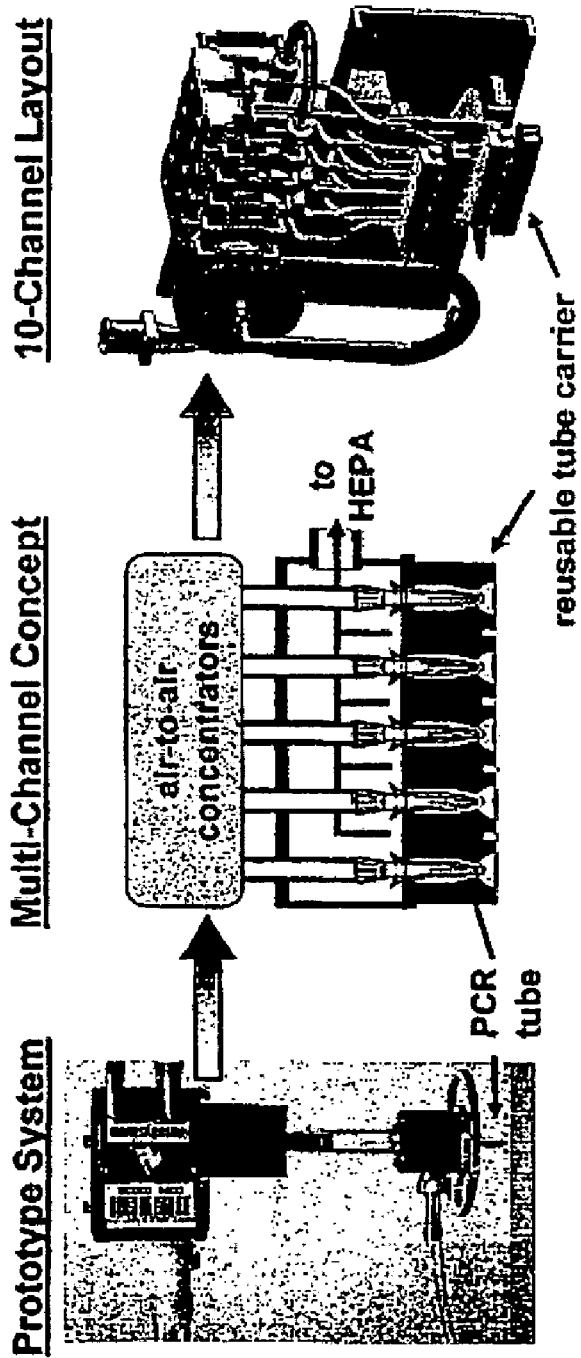
FIG. 6 illustrates a dry-impactor module for the optoelectronic sensor.

FIG. 6 shows an example of a dry-impactor module concept. In this example a single (e.g., prototype system) as well as a multi-channel device is illustrated, including individual sample tubes (e.g., PCR tubes) and tube carriers, in communication with air-to air concentrators from which the particle test sample is collected.

Figure 9:
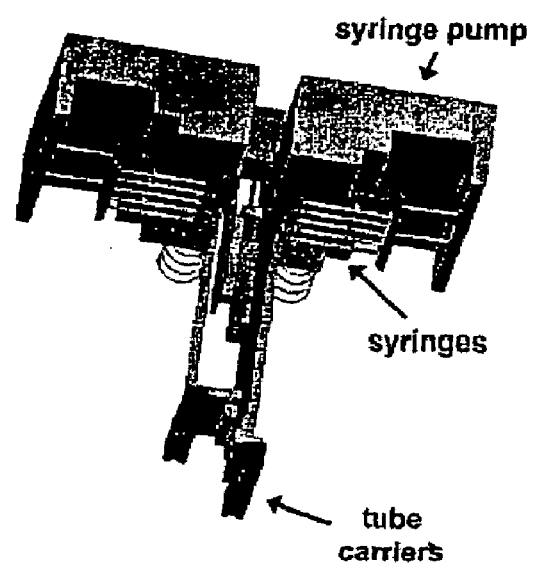
FIG. 9 illustrates an automated cell-delivery module for the optoelectronic sensor.

FIG. 9 shows an example of a cell-delivery that can be automated. The sensor cells (e.g., emitting cells) are introduced to the system by means of a syringe and syringe pump arrangement, which can include pipettors or other delivery equipment. This type of assembly allows for multiple and simultaneous introduction of sensor cells to the particle samples (e.g., samples in reaction chambers (e.g., tubes).

Figure 12:
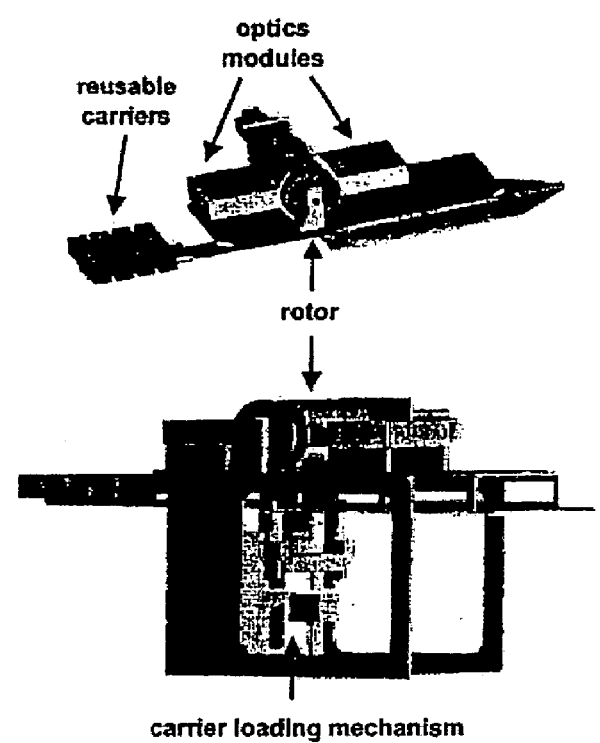
FIG. 12 illustrates an automated centrifuge module for the optoelectronic sensor.

FIG. 12 shows an example of a centrifuge module concept used to spin the particle samples or cell samples. Carriers having the sample tubes are introduced via a loading mechanism into a rotor assembly that is suitable for receiving the carriers. The rotor spins the samples. The rotor assembly is in communication with optics modules for signal collection (e.g., photon emission), and an indexed motor can be used to allow for alignment of the samples chambers with the detector (e.g., optics modules).

Figure 15:
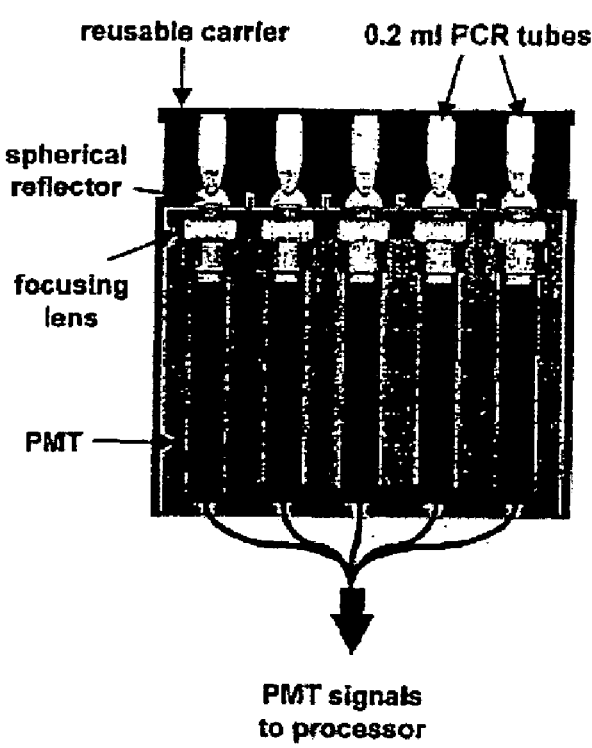
FIG. 15 illustrates an optics-photomultiplier (PMT) module for the optoelectronic sensor.

FIG. 15 shows an example of an optics module. Depending on the precise configuration, the module allows for a plurality of simultaneous testing of samples (e.g., in the reaction chambers, tubes). The carrier and tubes therein are introduced to the unit such that they are in communication with lens assemblies (e.g., integrated reflectors, lenses) if necessary, and ultimately a photodetector (e.g., a PMT). The PMT produces signals that are then sent to a processor for processing and display.

Figure 21:
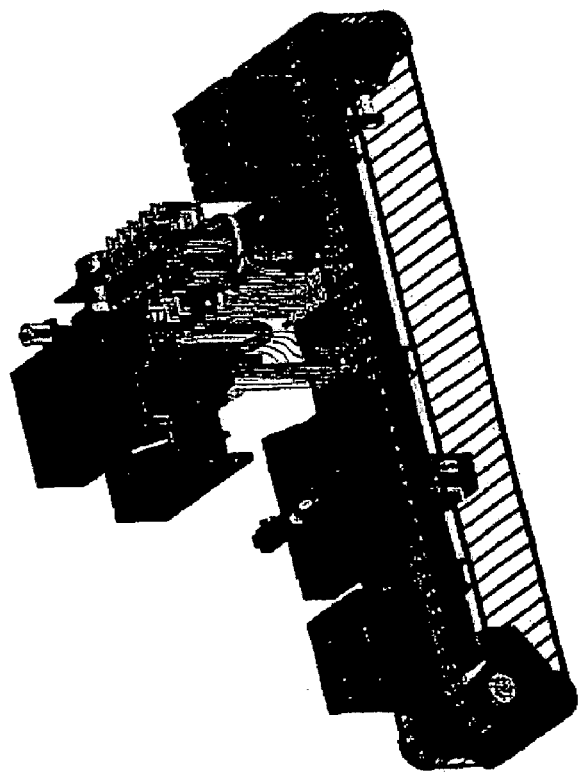
FIG. 21 illustrates an integrated dry-impactor/optoelectronic sensor

FIG. 21 illustrates an integrated dry-impactor/optoelectronic sensor. In this sensor the modules described above are assembled in a linear arrangement with a cassette holding 30 carriers deliverable to a belt-driven carrier transport module. This transport module moves the assay tubes sequentially from the collector to the cell delivery module to the centrifuge module, and finally to the confirmatory sample storage module following completion of photon detection. The overall size of this integrated sensor is approximately 54 inches wide by 33 inches high by 22 inches deep.

Real-world samples may contain substances that either inhibit the assay (false negative) or cause a response in the absence of specific antigen (false positive). In many instances, these samples can be treated prior to the assay to remove these substances. For example, soluble substances such as detergents or serum factors can be removed by pre-centrifugation step, where the agent is concentrated in the bottom of the tube and the liquid is replaced with assay medium (Portal Shield samples). Insoluble, large particulate substances can be removed from the sample by filtration, using commercial filters of a pore size (3–5 µm) that allows the passage of the agent, but retains the contaminant (diesel or soot samples). Samples can be processed rapidly through syringe filters, adding only a few minutes to the total assay time.

Specimen Localization

As part of the specimen collector or reaction chamber, different mechanisms (other than centrifugation) can be implemented to facilitate contact between emitter cells and candidate particles. For example, the use of electrophoresis, isoelectric focusing, dielectrophoresis, magnetically tagged particles, and the like in bioelectronic devices can be integrated into a system of the invention. See, e.g., U.S. Pat. No. 6,017,696 and other patents assigned to Nanogen, Inc.; Goater et al., Parasitology 117:S177–189, 1998; and U.S. Pat. Nos. 5,512,439 and 4,910,148 and other patents assigned to Dynal AS.

Mixing a aqueous sample containing target particles (particles here can be anything recognized by the emitter cells- proteins/toxins, viruses, bacteria, parasites, nucleic acids, etc.) with an aliquot of media containing emitter cells results in particle-cell contact leading to transient increase in the rate of photon emission. The time between the start of the mixing process and the maximum emission rate depends on the characteristic response of the particular cells to stimulation as well as the time over which the mixing occurs (the mixing time) and the typical time for the particles and cells to come into contact after mixing (the diffusion time).

Because a background rate of detected photons will exist even in the absence of target particles (background cell emission and thermal noise in the photon detector and its electronics, for example), photons emitted from single target-cell interactions can be difficult to distinguish from this background. To be useful as a signal, there must be a significant increase in the rate of photons detected over that of the background. For a given sample, this rate is maximized when the mixing time and diffusion time are minimized. Other possible signals that target particle are present in a sample include: an increase in the total number of photons detected in a period of time above that of the background alone, a change in the statistics of detected photons, or a change in the spectral qualities of the detected photons.

The diffusion time can be minimized by reducing the average distance between particle and cell after mixing. This can be accomplished by localizing the particles and/or cells to within a small volume, often a layer, within the larger mixed volume. However, the time to localize the particles and/or cells may be longer than the characteristic response time of the cells. (Mixing between particles and cells over this prolonged localization could produce a lower rate of photon emission, and therefore a lower signal, by increasing the average time between emissions.) To avoid this, one or both should be localized separately, while minimizing contact between them. This localization can also lead to a reduced mixing time.

Generally, the means to move particles or cells include the following:
sedimentation (by gravity or centrifuge)
fluid flow (forced or convective)
electric forces (electrophoresis and dielectrophoresis)
magnetic forces (using magnetic beads)
acoustics/ultrasonics (standing or traveling waves)

Localization requires a means of moving particles and/or cells combined with a barrier where particles and/or cells can collect, such as the solid surface of a channel or container, the surface of a filter, or the potential energy barrier surrounding an electric-field minimum. Examples include:
sedimentation (localizing cells on the lower surface of a chamber)
air impaction (impacted particles stick to or settle onto a collection surface)
filtering (particles or cells collect on to the surface or into the body of a filter)
affinity capture particles or cells can be localized through specific or non-specific binding interactions)
magnetic capture (magnetic beads held against a solid surface, a filter surface, or in the body of a filter by localized magnetic forces; beads may or may not have surface chemistry to promote attachment of particles or cells)
electrophoresis (charged particles only; collection on to an electrode surface)
dielectrophoresis (positive: collection of particles or cells on to an electrode surface; negative: collection into a region of minimum field)

Localization and mixing of particles and cells can be achieved by combining the above methods, as well as others. In the table below, examples of various localization/detector combinations are provided. Certain of the representative examples illustrate methods to localize particles or cells 2-dimensionally, allowing improvement in sensitivity or discrimination between different particles if an array of photon detectors (including a CCD) is used as opposed to a single photon detector (such as a PMT).

| Example | Method of localizing cells | Method of localizing particles | Mixing: particles or cells/ means | Detector |
| --- | --- | --- | --- | --- |
| centrifuge | centrifuge (short) | centrifuge (long) | cells/ sediment (cent.) | single |
| flow cell | sediment and attach to surface | shallow channel above cells | particles/ sediment (grav.) | single |
| flow cell (multiple cell lines) | sediment and attach to surface | shallow channel above cells | particles/ sediment (grav.) | imaging |
| flow cell/ magnetic bead | sediment and attach to surface | localized magnetic bead capture | particles (on beads)/ sediment (grav.) | imaging |
| flow cell/ electric field | sediment and attach to surface | shallow channel above cells | particles/ electrophoresis | single |
| tape/wick | flow (into wick) | air impact (tape) | cells/ sediment grav.) | single |
| air impact | centrifuge (short) | air impact (tape) | cells/ sediment (cent.) | single |
| Uniprep/ magnetic bead | sediment to surface | magnetic beads on filter surface | particles (on beads)/ sediment (grav.) | single |
| flow past cells | cells on filter surface | | particles/ flow past cells | single |

-continued

| Example | Method of localizing cells | Method of localizing particles | Mixing: particles or cells/ means | Detector |
|---|---|---|---|---|
| counter flow | cells held on filter surface by centrifugation | | particles/ flow past cells counter to cent. force | single |
| centrifuge tube filter | centrifuge onto filter surface | retained on filter surface | cells/ sediment (cent.) | single |
| dielectrophoretic trap | sediment and attach to surface | retained in flow by dielectrophoretic force | particles/ sediment (grav.) | single |
| traveling-wave dielectrophoresis | traveling-wave dielectrophoresis | traveling-wave dielectrophoresis | cells or particles/ traveling-wave dielectrophoresis | single |
| dissolvable-membrane tube | separate compartment | centrifuge (long) onto dissolvable membrane | particles/ dissolve membrane and sediment (cent.) | single |
| acoustic/ultrasonic | | | | |

LOCALIZATION EXAMPLES

In each of the following examples, it is assumed, unless stated otherwise: The sample is an aliquot of aqueous solution compatible with short-term cell life and function, possibly containing target particles (though the descriptions below will assume the presence of particles). An aqueous sample can be obtained from environmental, clinical, air-to-liquid, washed-swab, or other samples. An air sample can be obtained from a driven air stream (air sampler or surface pickup), electrostatic capture, or settled airborne particles. References to cells should be understood to mean emitter cells in an aqueous media that is compatible with their life and function. A particle and cell brought into contact is assumed to result in emission of one or more photons. A single or array photon detector exists external to the chamber in which the sample and cells are mixed, and there may be additional optical elements to enhance capture and detection of emitted photons (such as mirrors, lenses, lightpipes, etc.) either external or internal to the chamber. The chambers are either assumed to be transparent in part or in whole or to have another means to allow emitted photons to reach the detector.

Centrifuge

A sample can be centrifuged in a chamber for a time sufficient to sediment the particles. Cells can be introduced to the chamber without disturbing the particles and briefly centrifuged to sediment them onto the particles. Photon detection can occur during or, more typically, after the spin.

Affinity Capture (Surface Capture)

A sample can be introduced into a microcentrifuge tube, multi-well plate, filter unit, or other suitable device where some portion of the surface in contact with the sample has been modified to be able to bind and retain particles that may be present in the sample through specific or non-specific binding interactions. Non-specific binding may be facilitated via electrostatic/ion-exchange interactions, hydrophobic interactions, hydrophilic interactions, etc. Specific binding may be facilitated by immobilizing components to the surface that bind to substrates on the particles (e.g. antibodies, receptors, glycoproteins, proteins, peptides, carbohydrates, oligonucleotides, etc.), or by immobilizing components that are bound by receptors on the surface of particles (small molecules, peptides, proteins, carbohydrates, etc.).

Affinity Capture (Onto Mobile Substrate)

Similar to affinity capture on a surface, but particles are bound to mobile substrates (polymer beads, cells, charged molecules, magnetic beads, bacteria, etc.) that provide additional means of moving and/or localizing the particles or cells by various methods including those described herein.

Flow Cell

Emitter cells can be introduced to a shallow flow cell and allowed to attach to the bottom surface; non-adherent cells can be removed by additional flow. A sample is introduced, displacing much of the cell media, and particles can sediment out onto the attached cells. Photons are emitted as particles contact cells.

Flow Cell (Multiple Cell Lines)

Similar to the Flow Cell, with distinct regions of emitter cell sensitive to different target particles. Photon detection by imaging detector to allow identification of which cells are stimulated, and, therefore, which target particles are present in the sample.

Flow Cell (Magnetic Bead)

Similar to the Flow Cell. Appropriate magnetic beads are mixed with the sample, allowing target particles to attach to the beads. These decorated beads can be introduced to the flow cell where a strong localized magnetic field (due to a permanent magnet or electromagnet) captures them on the surface above the attached cells. Mixing can be initiated by either removing the magnetic force and allow the beads to sediment onto the cells, or moving the magnetic force to attract the beads to the surface to which the cells are attached.

Flow Cell (Electric Field)

Similar to Flow Cell, with the surface to which the cells attach and the one parallel to it being separate electrodes (at least one of which might be transparent). A sample can be introduced, displacing much of the cell media. An appropriate DC voltage is applied between the electrodes and the particles are moved to the attached cells by electrophoresis.

Tape/Wick

An air sample, possibly containing target particles, can be impacted on a transparent surface, which can be rigid or flexible (e.g., a tape), porous or nonporous. An absorbing material, or wick, can be attached, surrounding the impact area or, in the case of a porous surface, on the opposite side of that surface. Cells can be placed on the impact area, and, due to the wick, excess media will be absorbed, reducing the volume and depth of the media bearing the cells and bringing them closer to the particles. Cells sediment out onto the impacted particles or are, additionally, drawn toward them by flow if the surface is porous with the wick material behind.

Air Impact

An air sample, possibly containing target particles, can be impacted into a (fixed and initially empty) chamber which is suitable for centrifugation. Cells can be introduced to the chamber without disturbing the particles and briefly centrifuged to sediment them onto the particles. Photon detection can occur without, during, or, more typically, after the spin.

Filter Device/Magnetic Bead

A modified syringeless filter device, consisting of a chamber and a plunger with a suitable filter (e.g., WHATMAN® MINI-UNIPREP™, a plastic pre-assembled filtration device consisting of a 0.5 milliliter capacity chamber and a plunger which contains a filtration membrane at one end and a pre-attached cap/septum at the other, or similar), can be loaded with cells which are allowed to attach to the bottom surface of the chamber; unattached cells can be washed away. A sample can be introduced to the chamber along with magnetic beads with a suitable surface affinity. A modified plunger with a suitable magnet inserted inside and fixed near the back-side of the filter can be inserted into the chamber until the entrapped air escapes through the filter. This assembly can be inverted and (possible after a time to allow the beads to sediment onto the filter's surface) the chamber pushed down onto the plunger. Magnetic beads and particles can accumulate on the filter surface by filfration, sedimentation, and magnetic attraction. Particles can attach to the magnetic beads or be caught among them. Upon re-inverting the assembly, the particles, are held off the cells by the magnetic beads which, in turn, are held by the magnet inside the plunger. Removing that magnet releases the beads, and the particles, which sediment across the short distance onto the cells.

Flow Past Cells

One or more layers of cells can be allowed to sediment onto the surface of a suitable filter or membrane at the bottom of a chamber. A sample can be introduced to the chamber above the cells and pressure applied (by plunger or external pump, for example). As the sample flows past the cells, which are in intimate contact, particles are brought within close range of the cells, allowing contact.

Counter Flow

One or more layers of cells can be allowed to sediment onto the surface of a suitable filter or membrane at the bottom of a 'cell' chamber. A sample can be placed in a separate 'sample' chamber which is connected by some flow channel to the cell chamber at a point below the filter. The chambers can be arranged relative to one another such that, in a centrifuge, the sample chamber is closer to the axis of rotation; the level of the fluid in the sample chamber being closer to the axis of rotation than the fluid in the cell chamber. By this means, during the rotation of the centrifuge, fluid will flow between the chambers seeking a common distance from the axis of rotation. This can force some of the sample up through the filter supporting the cells and past the cells which are being held against that flow by the outward centrifugal force. As the sample flows past the cells, which are in intimate contact, particles are brought within close range of the cells, allowing contact.

Centrifuge Tube Filter

A sample can be introduced to the filter basket of a centrifuge tube filter with a suitable size cutoff. Under appropriate centrifuge conditions, the sample will be forced through the filter, accumulating particles larger than the filter's cutoff size on the surface of the filter. Cells can be added to the filter basket and be given a brief centrifugation to bring them onto the filter surface and the particles.

Dielectrophoretic Trap

Similar to the Flow Cell, but with suitable electrodes on any of the surfaces or projecting into the flow cell. A sample can be introduced by continuous flow past the electrodes, which can be connected to and electrically driven by and external source. For a suitable combination of flow rate, frequency, waveform, and amplitude, particles can be guided to and captured in a region of minimum electric field intensity above the cells by negative dielectrophoresis. After stopping the flow and changing the electrical drive to the electrodes (possibly including a DC voltage on between some electrodes to create an electrophoretic force), the particle can sediment or be driven (by electrophoresis or positive dielectrophoresis) onto the attached cells.

Traveling-wave Dielectrophoresis

In a shallow cylindrical chamber, suitable electrodes (perhaps transparent) can be fabricated on one or both of the parallel faces, including a central planar electrode to collect particles, an electrode around the periphery, and a set of spiral electrodes (either on the same surface as the central one or the opposite surface). A sample can be introduced to the chamber, and a DC potential applied between the peripheral and central electrodes to attract the particles to the central electrode by electrophoresis. By an exchange of fluids, cells can be introduced to the chamber. Energizing the spiral electrodes with the appropriate phase-shifted AC voltages can sweep the cells to the center by traveling-wave dielectrophoresis, where they can sediment onto the particles.

Dissolvable-membrane Tube

Use can be made of a electrically-actuated dissolvable gold membrane to maintain isolation between target particles and emitter cells during the localization of the particles by centrifugal sedimentation. Either the particles can be sedimented onto a membrane over the cells (as shown in FIG. 20), or the cells can be held off from the bottom of the chamber by a membrane spanning the bottom of a separate chamber (perhaps an insert). In either case, after the membrane has be dissolved by electrical activation, the particles and cells are mixed by sedimentation, possibly centrifugal.

Acoustics/Ultrasonics

Concentration of particles may be accomplished using acoustic or ultrasonic signals. Particles can accumulate at nodes in a sanding wave pattern, or be move by a traveling-wave pattern. Cells can also be moved this way, or delivered by any of several means discussed above.

Toxin Detection

In order to detect monovalent antigens, it is necessary to induce crosslinking of surface antibodies using one of two general strategies. First, one can express two independent binding sites on the cell surface, such that two receptor molecules can bind to a single ligand. Alternatively, one binding site can be expressed on the cell surface if the ligand is presented to the cell in a manner in which it appears to be polyvalent. The following are specific examples using the model of antibody-antigen recognition.

First, two antibodies can be expressed on the surface of a single cell line, each specific for different epitopes of a individual molecule (epitopes 1 and 2). The binding of a single molecule to two antibodies (one antibody against epitope 1 and another antibody against epitope 2) would initiate crosslinking and light emission. More specifically, a single B-cell line is engineered to express two independent antibodies, each recognizing a different epitope on a single molecule. The presence of monomeric antigen is now capable of crosslinking the surface antibodies, resulting in increased intracellular $Ca^{2+}$ and emission of light by aequorin. We currently have a cell line that expresses functional antibodies against both *Y. pestis* and *F. tularensis* (in addition to the endogenously expressed PC antibody). Each of these agents is recognized independently by this cell line, indicating that both antibodies are functional and demonstrating that B-cells are capable of expressing two functional antibodies simultaneously.

Another potential issue is the sensitivity of the optoelectronic device and methods with an antigen that cannot be pelleted using centrifugal force. The *Yersinia pestis* F1 antigen exists as a low molecular weight polymer in solution, and is therefore not sedimentable in our assay. However, B-cells expressing antibody against F1 are capable of detecting soluble F1 antigen at 5 ng/ml. This compares favorably with current immunoassay techniques and demonstrates that the optoelectronic device can be quite sensitive to soluble agents. A complementary experiment was carried out using phosphorylcholine antigen conjugated to ovalbumin. The ability of this small antigen to stimulate antibody crosslinking on the cell surface indicates that this low molecular weight antigen, containing multiple copies of PC epitopes, is able to effectively crosslink surface antibodies and generate calcium influx and photon emission.

A second strategy can improve the limit of detection for monovalent antigens shown above by taking advantage of the centrifugal format. This approach utilizes a scheme where one of the toxin antibodies is expressed on the surface of benign bacteria and the second antibody on the surface of B cells. The toxin can now be sedimented by centrifugation, and B cells expressing the second antibody added. Because multiple antigens are immobilized on the surface of the bacteria, the toxin will in essence appear polyvalent to the B-cell, and will initiate a crosslinking event and photon emission. More specifically, Antibody against epitope 1 of a monomeric antigen (e.g. toxin) is expressed on the surface of bacteria. Soluble toxin binds to these antibodies, coating the bacteria with toxin antigen. These toxin-coated bacteria are sedimented by centrifugation prior to addition of B cells expressing antibody against epitope 2. Crosslinking of the B-cell antibodies results in light emission by aequorin. Experimental results on this strategy demonstrate the feasibility of detection of bacterial surface antigens, and the increased sensitivity resulting from sedimenting those bacteria prior to the addition of B cells. Similar approaches can also be used for any poorly sedimenting agent to improve its presentation to B-cells.

Multiplexing Assays

The following is a description of how B-cell mixtures could be used to increase the number of detectable antigens without increasing the number of detection channels (tubes, etc). The simplest way to detect multiple analytes is to use a single B-cell line per detection channel and to increase the number of cell assays by increasing the number of detection channels. This is acceptable for small numbers of assays but, as increasing numbers of analytes are added, the process becomes more complex and resource intensive. It is possible, however, to conduct up to 31 tests with concurrent negative controls in only a 5-channel system if different B-cell lines are mixed together.

As an example, if one has a single channel, one can at most detect a single B-cell assay. If, however, one has two channels, then one can detect 3 separate assays, where each channel contains an equal mixture of 2 of the 3 separate B-cell lines:

For example, if one has 3 B-cell lines: A,B,C

And one mixes them into two channels thusly —

| | |
|---|---|
| Channel 1: A, B | Channel 2: B, C |

Then there are three positive readout possibilities:

| Channel 1 | Channel 2 | |
|---|---|---|
| Yes | No | implies only A is present |
| No | Yes | implies only C is present |
| Yes | Yes | implies only B is present (or that more than one agent is present, which we will consider unlikely for now) |

Similarly, if one has 3 channels, one can detect 7 independent assays, by mixing groups of four cell lines together—

(A convenient shorthand will hereafter be utilized where the cell lines for individual agents are labeled A through a letter corresponding to the number of cell lines, and the channel numbers will be written to indicate what channels are required to detect positively for each individual agent as follows—123: F—means channels 1, 2, and 3 must all register positive to ID agent F)

| Channel 1 | Channel 2 | Channel 3 |
|---|---|---|
| A, B, G, F | B, C, E, F | C, D, G, F |
| 1: A | 12: B | 123: F |
| 2: E | 13: G | |
| 3: D | 23: C | |

A formula embodying the relationship that simply describes the number of independent assays that can be accessed by a given number of channels, assuming all assays are mixed in equal proportion is:

Cell assays=$2^n-1$ where n is the number of channels and the number of cell assays that need to be mixed in each channel is given by $2^{(n-1)}$.

Thus, to mix 16 different B-cell lines together, 5 channels are needed to interrogate 31 different assays. The design for a 10-channel system could, in fact, be used to provide ID for 31 separate agents with concurrent negative controls (5-channel positive ID, 5-channel negative control).

The channel mixtures and positive detection correlation for a 4-channel system (15 different assays) is shown below:

| Channel 1 | Channel 2 | Channel 3 | Channel 4 |
|---|---|---|---|
| A, B, G, F, I, K, L, M | B, C, H, I J, L, M, N | F, C, D, I J, K, M, O | D, E, G, H J, K, L, M |
| 1: A | 23: C | 123: I | 1234: M |
| 2: N | 24: H | 234: J | |
| 3: O | 34: D | 134: K | |
| 4: E | 12: B | 124: L | |
| | 13: F | | |
| | 14: G | | |

Without further elaboration, it is believed that one skilled in the art can, based on the above disclosure and the examples below, utilize the present invention to its fullest extent. The following examples are to be construed as merely illustrative of how one skilled in the art can practice the invention, and are not limitative of the remainder of the disclosure in any way. All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

FIG. 1 is a schematic diagram showing the general cellular components of the invention. A cell (here a B cell) that contains an emitter molecule (here aequorin) has antibodies present on its surface. These antibodies are specific for an antigen on a target particle, such as a biological warfare agent. Binding of the target particle to antibodies on the B cell brings two or more antibodies close together on the cell surface, causing a signal transduction cascade that leads to release of calcium from intracellular stores into the cytoplasm. This increase in cytoplasmic calcium concentration causes aequorin to emit a photon. The photon is then captured and registered by a photo multiplier device, such as a CCD. Thus, a cellular biosensor can be implemented using cells having functional surface antibodies and containing a cytoplasmic emitter molecule that responds to increased calcium concentration.

Such a cell-based detection system provides rapid, sensitive, specific, accurate, and flexible detection of any antigen on any target particle. In regard to flexibility, the system can be modified to target any particle or groups of particles. In one example, a single emitter cell can contain a plurality of antibody types, each type being specific for non-overlapping groups of target particles. This single emitter cell can then be used to identify a genus of target particle species at once.

In a second example, a reaction chamber can contain two types of emitter cells. One type of emitter cell contains antibodies that are specific for a genus of target particles (e.g., bacteria) and emits a photon of a first wavelength in response to contact with any member of the genus. The second type of emitter cell contains antibodies that are specific for a particular species within the genus (e.g., *Yersinia pestis*) and emits a photon of a second wavelength different from the first wavelength in response to contact with the species. This arrangement offers extremely high accuracy by reducing or eliminating false positive signals. Only when photons of the first and second wavelength are detected, would a positive event be registered. This nesting of emitter cell specificities can be extended to more than two levels as necessary to reduce or eliminate false positive signals.

FIG. 2 is a schematic diagram of a general architecture and use environment for the invention.

FIG. 3 is a schematic diagram of the molecular biology employed in one embodiment of the invention. In this example, a universal B cell line that expresses an emitter molecule (e.g., aequorin) but does not express antibodies becomes the basis for generating B cells that can express any antibody specific for any antigen. An antibody expression vector is introduced into the universal B cell, selected for the presence of the expression vector, and expanded for use in a detection system of the invention. Using this strategy, in conjunction with pDisplay and VKExpress (described in "Antibodies" section above), target-specific emitter cells were generated for a variety of targets. Emitter cells specific for Foot and Mouth Disease virus (FMDV), Venezuelan Equine Encephalitis (VEE) virus, *Yersinia pestis, Francisella tularensis*, Brucella spp., the O1 and O139 strains of *Vibrio cholera*, and orthopox viruses have been produced. The cDNA and sequence for the FMDV antibody variable regions were obtained from the USDA. The cDNAs and sequences for the *Yersinia pestis, Francisella tularensis*, Brucella spp., the 01 and 0139 strains of *Vibrio cholera* antibody variable regions were obtained from investigators at NMRC. The variable regions of the VEE and orthopox antibodies were cloned from hybridomas obtained from the CDC and USAMRIID, respectively. Foot and Mouth Disease Virus (FMDV), *Yersinia pestis, Francisella tularensis*, and Venezuelan Equine Encephalitis Virus (VEEV) are responsible for Foot and Mouth Disease, the Plague, tularemia, and encephalitis, respectively. Cloning from the hybridomas was done with a combination of primers described in several published articles. Emitter cells specific for *Bacillus globigii* are being produced because this non-pathogenic bacterium is used by some military agencies as a test organism in field trials of biological warfare agent detection systems. FIG. 5 includes a line graph showing the photon emission response when several clones of FMDV-specific emitter cells were contacted with live FMDV targets. In each case, the emitter cells fired photons within about 20–30 seconds after contact between the target and the cells. Included in the graph is data showing a lack of emission when a mutant FMDV (having single amino acid mutation in the viral coat protein) that would not be expected to bind to the emitter cell was contacted with an emitter cell clone. The negative control supports the high specificity that is built into the detection system.

Various configurations of a centrifuge and photomultiplier tube (PMT) arrangement can be incorporated into a system of the invention. The arrangement includes a rotor (motor) that spins a sample microfuge tube from a swinging harness and includes a balance tube in a fixed position. The PMT is shown at the bottom, facing upwards toward the bottom end of sample tube at rest. In a typical experiment for a target particle that is smaller than the emitter cell, the particle-containing liquid sample is placed in the sample tube and centrifuged under conditions sufficient to sediment the majority of the particles to the bottom of the tube (e.g., 60 seconds at 5600×g for *Francisella tularensis*). A suspension of emitter cells is then layered onto the sample in the tube (so as not to disturb the sedimented particles) and spun briefly to pellet the cells into contact with the target particles. If target particles are present in the candidate particles, photons of a specific wavelength should be emitted from the cells and captured and registered by the PMT.

In specific embodiments, the PMT can be a Hamamatsu HC 125–08 PMT interfaced with a Stanford Research systems SR400 Two Channel Gated Photon Counter. The centrifuge can be a Sapphire 17 turn, 18.5 AWG, 5 amp motor having a swinging bucket configuration.

Figure 20:
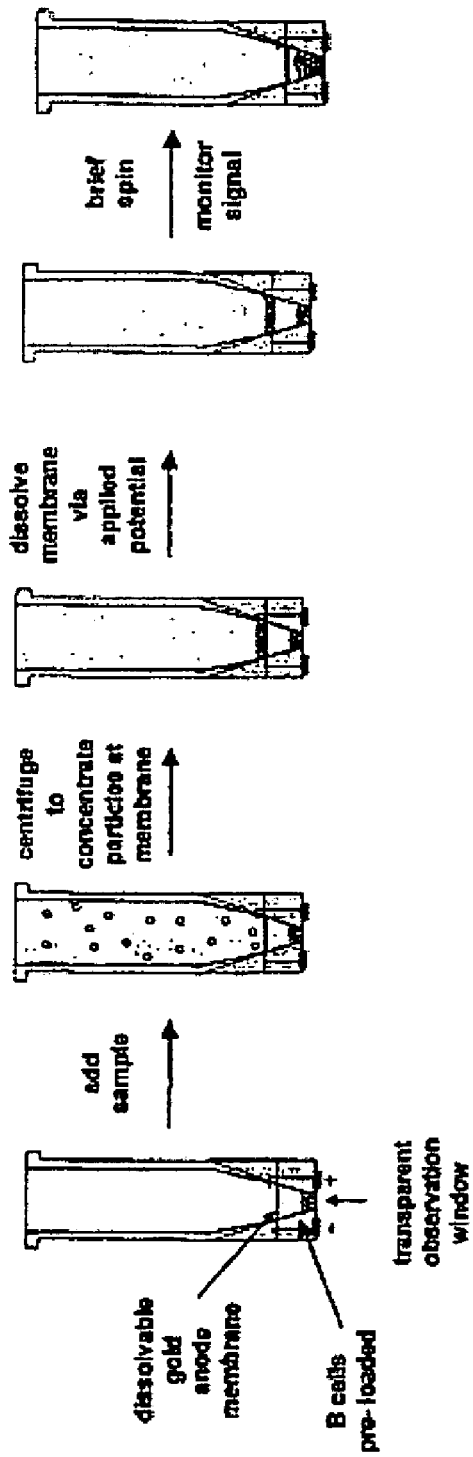
FIG. 20 is a schematic of a custom tube for the optoelectronic sensor.

The centrifuge tube (reaction chamber) can be altered and upgraded as needed to aid contact between candidate particles and the emitter cells. In one embodiment shown in FIG. 20, the tube contains an enclosed compartment that holds pre-loaded emitter cells at the bottom of the tube. This compartment is separated from the rest of the tube by a dissolvable gold anode membrane. In operation, a same containing candidate particles is deposited into the tube and spun to concentrate candidate particles at the membrane. The membrane is then dissolved, and the tube briefly spun to contact the particles with the emitter cells. This dissolvable membrane system is described by Langer and colleagues in Angewantde Chimie International Edition 39:2396–2407, 2000; and Nature 397:335–338, 1999.

The steps in the centrifuge process can be automated or alternatively designed so that the user need not stop the centrifuge at all. For example, the introduction and removal of liquids and samples can be accomplished without the need to stop the rotor by adapting the mechanical features of preparative centrifuges (e.g., ultracentrifuges) available from Beckman Instruments. In addition, it may be desirable to detect photon emission while centripetal forces are still being applied (e.g., when the contact between emitter cells and target particles are unstable without centrifugation). To detect photons emitted from the sample tube while it is spinning, the PMT can be arranged in a radial position relative to the rotor axis. In most cases, the PMT in this arrangement need not be spinning along with the sample tube, but instead can be stationary and simply register emission of photons when the sample tube passes in front of the PMT. If the emission signal is very weak, then the detector (e.g., PMT, a CCD chip) can be coupled to the rotor and spun along with the sample tube. Alternatively, multiple PMrs can be arrayed around a circumference of a rotor for detecting emissions.

If multiple samples are spun on the same rotor, the positioning or signal processing of the PMT can be altered if necessary. In one embodiment, the rotor accommodates 4 sample tubes, each containing cells that emit at the same wavelength. To differentiate emissions originating from one sample over the emissions from another, a single radially aligned PMT can detect emissions continuously. The continuous emission data is then resolved using a timing trace from the rotor, which monitors the position of each sample over time, to allocate the emissions to each sample. Other variations are understood to be within the invention.

Figure 17:
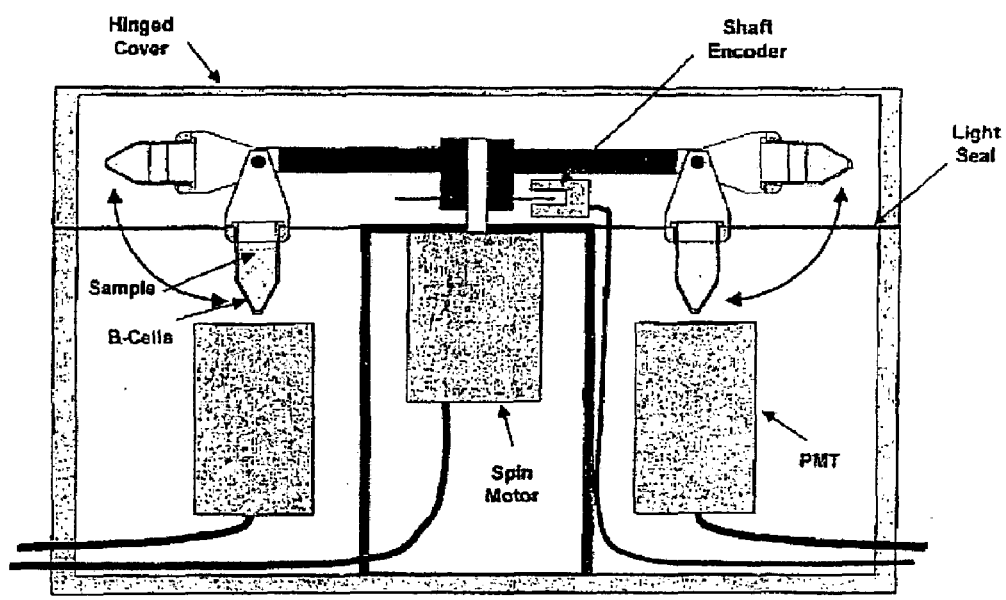
FIG. 17 is a schematic illustrating a multi-channel centrifuge in the optoelectronic sensor.
Figure 18:
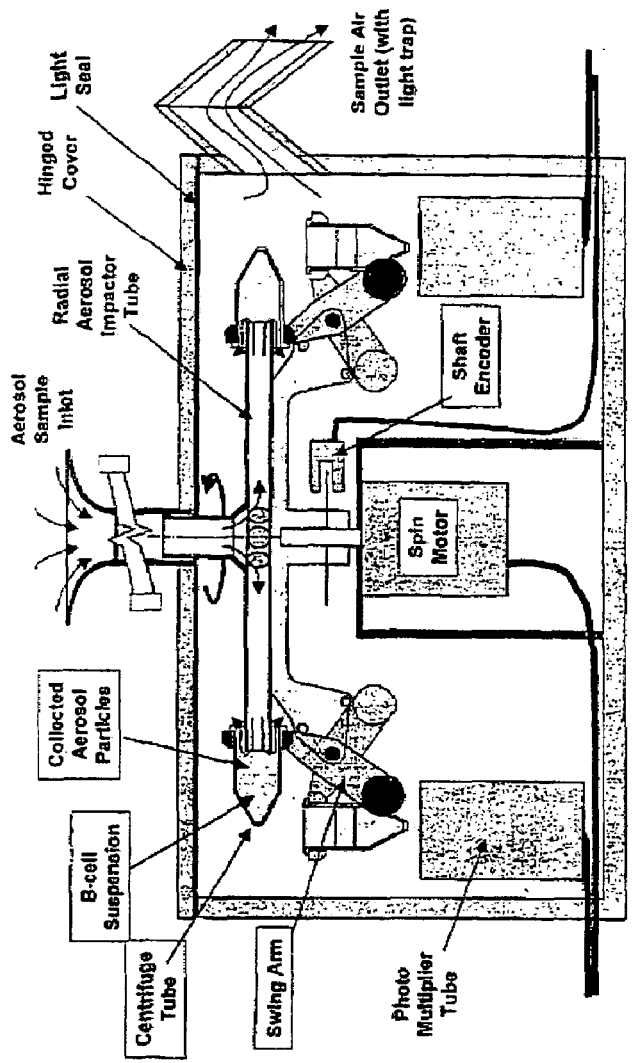
FIG. 18 is a schematic illustrating a wet centrifuge/impactor concept in the optoelectronic sensor.
Figure 19:
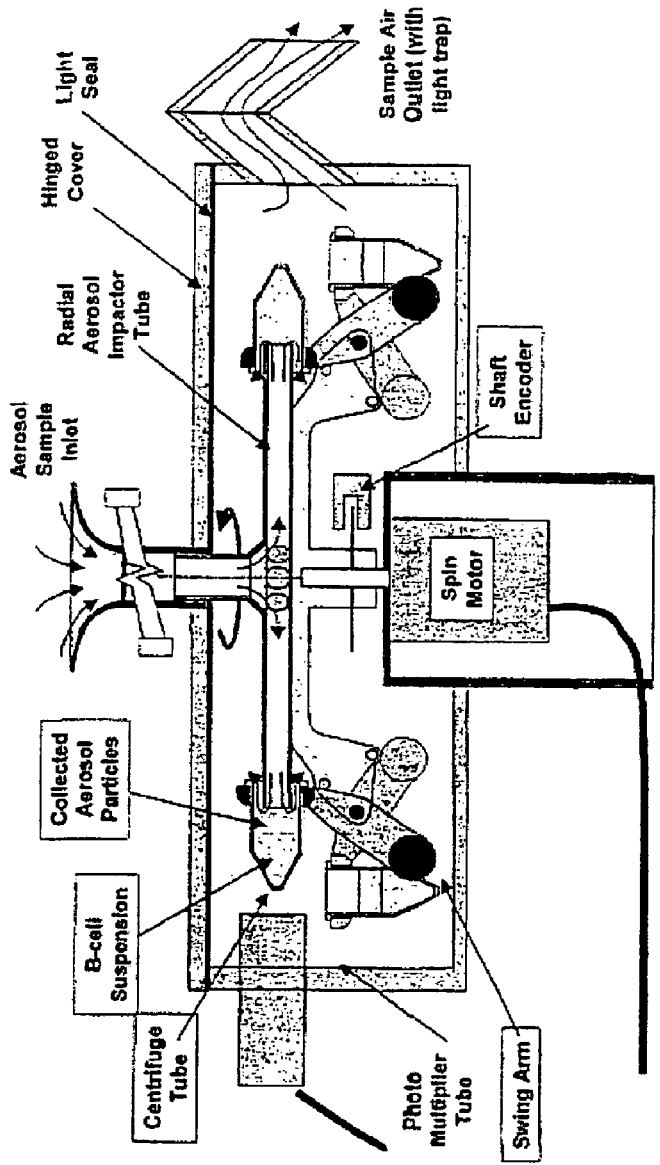
FIG. 19 is a schematic illustrating a wet centrifuge/impactor concept in the optoelectronic sensor.

For example, FIG. 17 is a schematic drawing of two reaction tubes coupled to a rotor, with two PMTs aligned below the tubes. At a resting position, the rotor positions each of the tubes below the corresponding PMT, using the rotor position encoder. In another example, the centrifuge system shown in FIG. 17 can be integrated with an air sample collector to achieve the system shown in FIG. 18. The radial aerosol impactor tube can include any type of particle monitor, such as described in U.S. Pat. No. 5,932, 795 and references cited therein. In still another example, the system described in FIG. 18 can be altered so that only one PMT aligned radially in relation to the rotor axis is required, as shown in FIG. 19. As discussed above, emissions registered by the PMT are resolved for each sample tube using the shaft encoder.

Referring back to FIG. 17, fluid components including, but not limited to, suspensions of B cells engineered to recognize specific bioagents, buffer solutions, preservatives, cell culture medium, can be placed in each of several centrifuge tubes, mixed with a liquid suspension of the sample particles that has previously been collected from aerosol samples in a separate process particles may include but are not limited to, proteins, peptides, chemicals, viruses, bacteria in vegetative and spore forms, fungal spores, pollen grains, protozoa, blood or tissue derived cells, and fragments thereof either alone or in conjunction with carrier particles such as dust). When the spin motor is started, the centrifuge tubes swing out into a radial position, and the B cells and/or sample particles are driven to the bottom of the centrifuge tubes at rates depending upon the size and density of the particles. The exact sequence whereby cell and sample-containing fluids are added and centrifuged can be customized based on their relative sedimentation velocities to maximize signal. In general, it is expected that maximum photon output can be obtained from particles that sediment more slowly than B cells by spinning these samples (a pre-spin) for appropriate times before the addition of B cells and spinning to bring them into contact. For particles sedimenting at similar or faster rates than B cells, a single spin of the mixed sample and B cell components will initiate maximal photon output from the system. Data from particle size analyzers (including but not limited to BAWS units, and fluid particle analyzers) incorporated upstream of the centrifugation device can be used to automatically determine the optimal operation sequence and initiate appropriate computer-controlled automated sample handling.

When the "spin cycle" is terminated and the rotor comes to a controlled stop in a pre-determined position controlled by the spin motor and shaft encoder, the swing arms rotate under gravity forces so that the bottoms of the centrifuge tubes are presented to the sensitive surface of the photomultiplier tubes, and any light signals are then recorded. In a modified version of this implementation, a single photomultiplier tube can be positioned at the maximum radius of the rotor/tube configuration and used to collect photons from each tube as they pass by the sensitive surface of the photomultiplier tube in succession. The photon output measured from individual tubes can be assigned and combined based on the monitoring of the shaft encoding system.

Referring back to FIG. 18, the process of collection of the aerosol particles is integrated with the process of bringing the aerosol particles into contact with the B-cells. Here, the centrifuge tubes are attached to swing arms that allow them to cover the ends of radial impactor tubes while spinning, and the aerosol sample is induced to flow into the sample inlet by the centrifugal forces acting on the air in the rotating radial impactor tubes (can be assisted as necessary by additional blower units). The high velocity of the flow causes aerosol particles to impact on the inner surface of the centrifuge tube or the surface of a liquid contained in the tubes and results in the capture of the particles on the surface of the tube or in the liquid, respectively. When a liquid is present, centrifugal pressures acting on the liquid will balance the force imparted by the high velocity air flow required for particle capture in the liquid and prevent it from being blown out by the impacting air. The aerosol particles are retained following impact with the tube surface or liquid and in the case of liquid collection, forced to flow radially outward thereby providing increased local particle concentrations at the maximum radius (the bottom of the centrifuge tube). Addition of B cells and spinning them into the locally concentrated particle zone following the collection phase will initiate photon output. Alternatively, the B cells can be present in the fluid during collection and light output monitored in real time while spinning with a single photomultiplier tube (FIG. 19). In a modified version of this implementation, the fluid components (including but not limited to particle samples collected via an alternative bioaerosol collector, and suspensions of engineered B cells) could be added to the inlet(s), and the centrifugal forces can be used to distribute them to the tubes.

When the "spin cycle" is terminated and the rotor comes to a controlled stop in a pre-determined position controlled by the spin motor and shaft encoder, the swing arms rotate under gravity forces so that the bottoms of the centrifuge tubes are presented to the sensitive surface of the photo multiplier tubes, and any light signals are then recorded. In a modified version of this implementation, a single photomultiplier tube can be positioned at the maximum radius of the rotor/tube configuration and used to collect photons from each tube as they pass by the sensitive surface of the photomultiplier tube in succession. The photon output measured from individual tubes can be assigned and combined based on the monitoring of the shaft encoding system.

Figure 7:
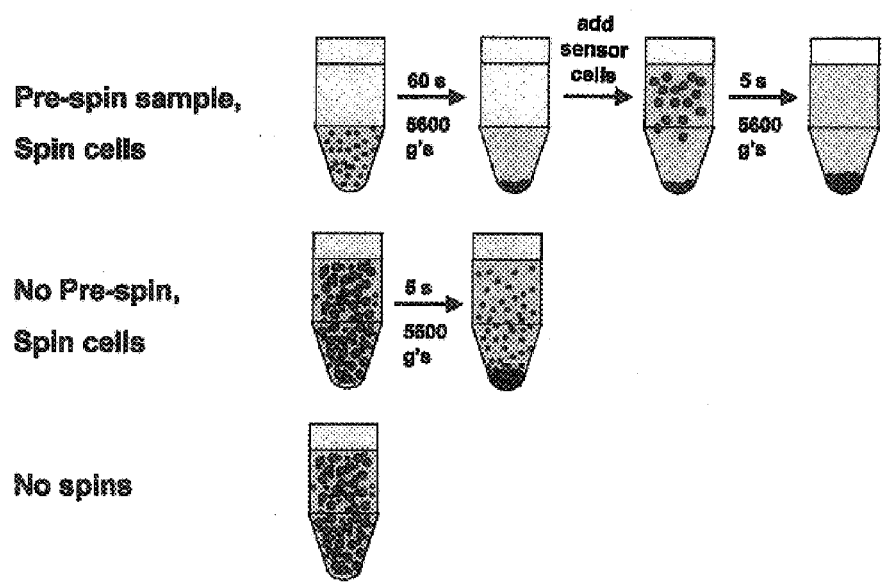
FIG. 7 is a schematic illustrating the effect of localization and mixing.

FIG. 7 is a schematic representation of the results of sequential centrifugations. For target particles smaller than emitter cells but having the same density of emitter cells, it is beneficial to first spin the candidate particles (e.g., at high speed) to pellet them. Thereafter the emitter cells can be added and spun under conditions which can be milder to prevent reduction of their responsiveness as needed (top series). In addition, this sequence of centrifugation forces almost all candidate particles and emitter cells into a relatively small volume at the bottom of a centrifuge tube. In contrast, mixing the candidate particles and the emitter cells together and spinning them at one time will lead to separation rather than contact between the particles and emitter cells (middle series). Of course, no spin at all dramatically reduces the effective concentration of particles and emitter cells in the reaction (bottom series).

Figure 8:
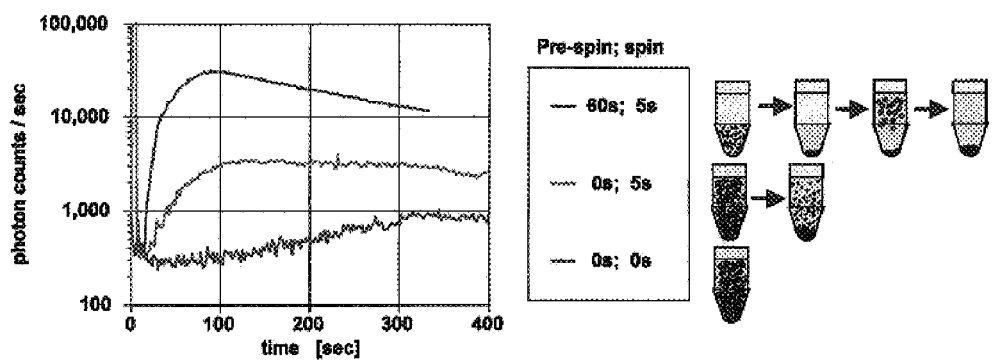
FIG. 8 illustrates the effect of localization using tularemia cells.

FIG. 8 includes a line graph showing in an actual experiment confirming the consequences proposed in FIG. 7. Emitter cells specific for *Francisella tularensis* were mixed with killed *Francisella tularensis* cells in the three methods shown in FIG. 7. As seen in the line graph, the sequential spin method resulted in fast and efficient emission after contact. In contrast, the emission profile of the single spin method was far less pronounced in both timing and magnitude. The no-spin method barely exhibited a reaction.

A similar emission profile was generated in a separate experiment, as summarized in the line graph shown in FIG. 8. Inspection of the emission traces suggested that the single spin method resulted in target-specific emissions a little quicker than the two-spin method. However, this result was found to be primarily an artifact of the longer spin required for the two-spin method and does not reflect an actual improvement in the response time of the B cells. In fact, the initial slope of the two-spin method was significantly greater than that for the single spin method, indicating that the two-spin method led to a robust emitter response.

Figure 10:
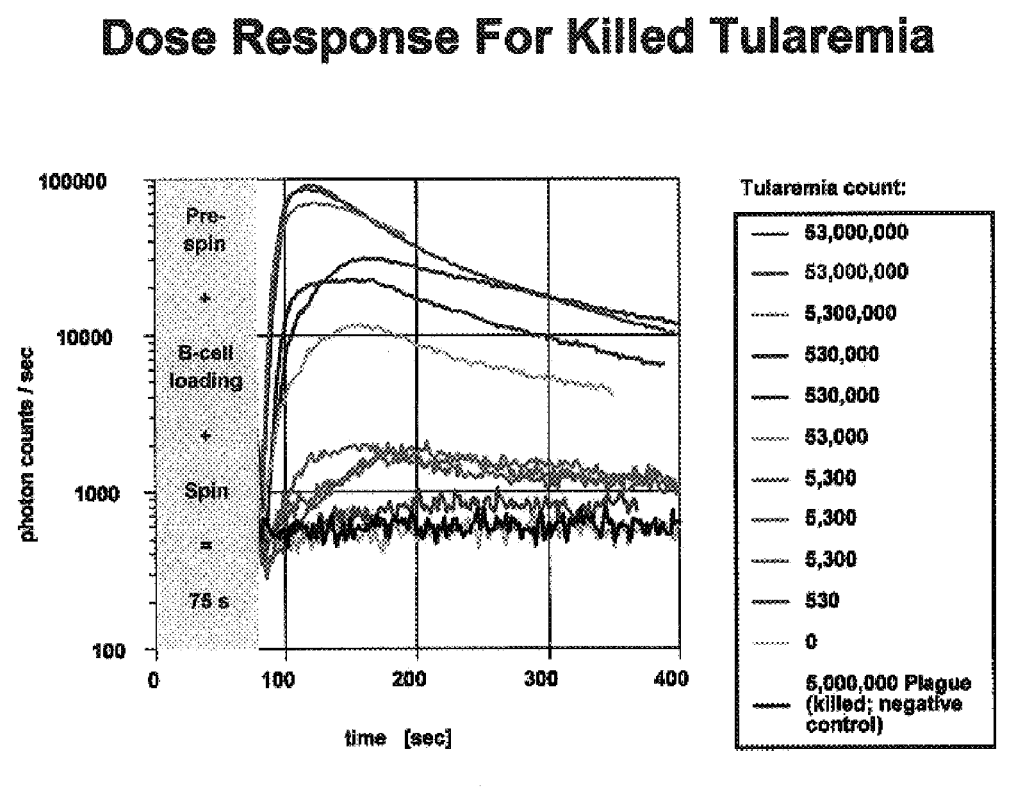

The sensitivity of the detection system shown in FIG. 8 was evaluated by titrating the number of tularemia cells deposited into the centrifuge tube. The results are summarized in the line graph shown in FIG. 10. It appears that 25,000 emitter cells were capable of emitting photons detectable above background in response to about 5,300 tularemia target particles. It is expected that further optimization of reaction conditions will increase sensitivity.

Cell responses are improved after a single freeze-thaw cycle (see FIG. 22). In this experiment, cells specific for *Yersenia pestis* (YP) were centrifuged, resuspended in freezing medium (RPMI with 10% DMSO and an additional 10% FBS), frozen at −80° C., and transferred to liquid nitrogen. Cells were thawed at 37° C. and 1 ml ($2 \times 10^6$) cells were diluted into to 4 mls of RPMI and incubated overnight at 37° C. The following day the cells were loaded with coelenterazine for 2 hours, washed into $CO_2$—Independent medium ($CO_2$—I) and recovered for 24 hours. 10,000 cells were challenged with $5 \times 10^5$ YP (50 ul of YP at $10^7$/ml). Untreated cells displayed a response of 9500 photons per second, while frozen thawed cells emitted approximately 6 fold more photons in response to YP. This stimulatory effect could be largely replicated by exposing the cells to freezing medium, without the actual freezing (5 fold stimulation). It appears that the stimulatory factor in the freezing medium is the DMSO. When cells were treated with 2% DMSO (the final concentration of DMSO when 1 ml of cells in freezing medium containing 10% DMSO is diluted into 4 mls of normal medium) a similar level of stimulation was detected. The DMSO effect may be due to a number of factors. DMSO is known to effect hematopoetic cell differentiation, and may be stimulating the cells through this pathway. Additionally, cells frozen in medium containing glycerol also show similar levels of stimulation. Thus, it appears that the effect can also in part be due to a stress response induced by the DMSO and it can be possible to replicate this stimulation using any of a number of conditions that stimulate a "heat shock" response.

The cells can be stored frozen in the coelenterazine-charged state. Cells were loaded with coelenterazine, allowed to recover for 24 hours, and then frozen. Upon thawing the cells were washed through 10 ml of $CO_2$—I medium and the cells were resuspended in $CO_2$I medium to a concentration of $5 \times 10^5$ cells/ml. These cells were capable of detecting YP (in this case about 1 hour after thawing, but shorter times are possible). These cells remained capable of detecting agent for several days when stored at RT. Pretreatment of these cells with DMSO, prior to loading with coelenterazine and freezing, can increase the sensitivity of the cells to agent after thawing.

In FIG. 22, cells were challenged with 50 ul of 10,000,000 YP/ml diluted in $CO_2$—I after various cell treatments. Untreated: Cells were grown in RPMI, loaded with coelenterazine, washed, recovered for 24 hours, and challenged with YP. Freeze/Thaw: Cells were grown in RPMI, transferred to freezing medium, and frozen. Thawed cells (1 ml) were placed into 4 mls of RPMI and incubated at 37° C. for 24 hours, loaded with coelenterazine, washed, recovered for 24 hours, and challenged. Freezing Medium: Cells were grown in RPMI, transferred to freezing medium and incubated at RT for 10 minutes. Cells (1 ml) were placed into 4 mls of RPMI and incubated at 37° C. for 24 hours, loaded with coelenterazine, washed, recovered for 24 hours, and challenged. 2% DMSO: Cells were grown in RPMI, transferred to RPMI containing 2% DMSO and incubated at 37° C. for 24 hours, loaded with coelenterazine, washed, recovered for 24 hours, and challenged.

Figure 11:
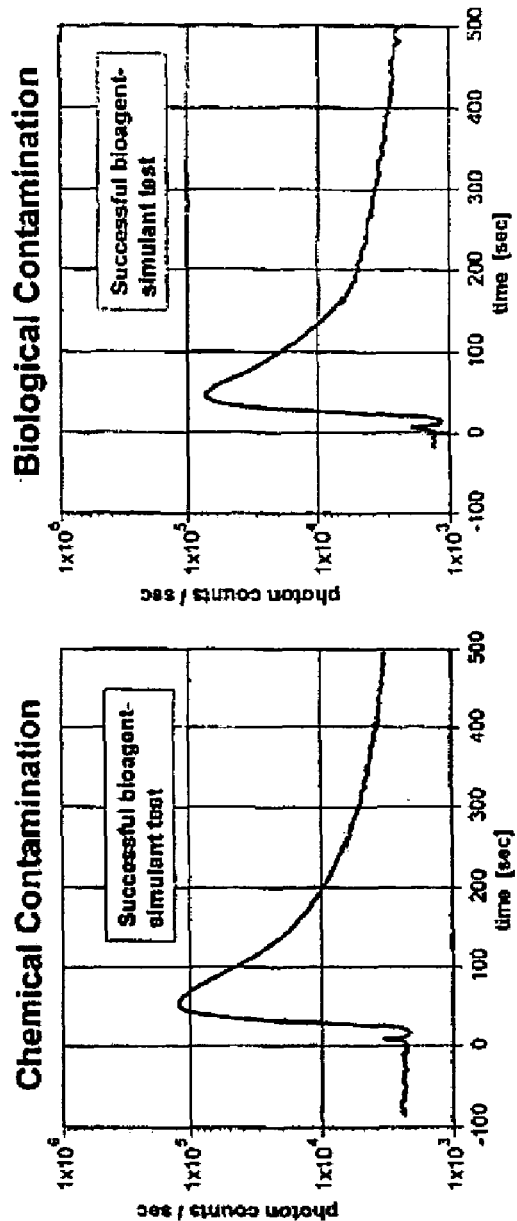
FIG. 11 illustrate B-cell resistance to chemical and biological contamination.

A successful biological warfare detection system should be resistant to contamination by common environmental substances present on a battlefield. To evaluate whether emitter cells can operate under environmental stress or contamination, emitter cells were mixed with a target particle after exposure of the emitter cells to one hour of full strength diesel exhaust (left line graph in FIG. 11), or when the emitter cells were contaminated by $10^7$ *E. coli* (right line graph in FIG. 11), which was used as a surrogate contaminant for any field bacterium. As shown in FIG. 11, the particular chemical and biological contaminants tested did not affect the ability of emitter cells to fire photons in response to a target particle.

Figure 13:
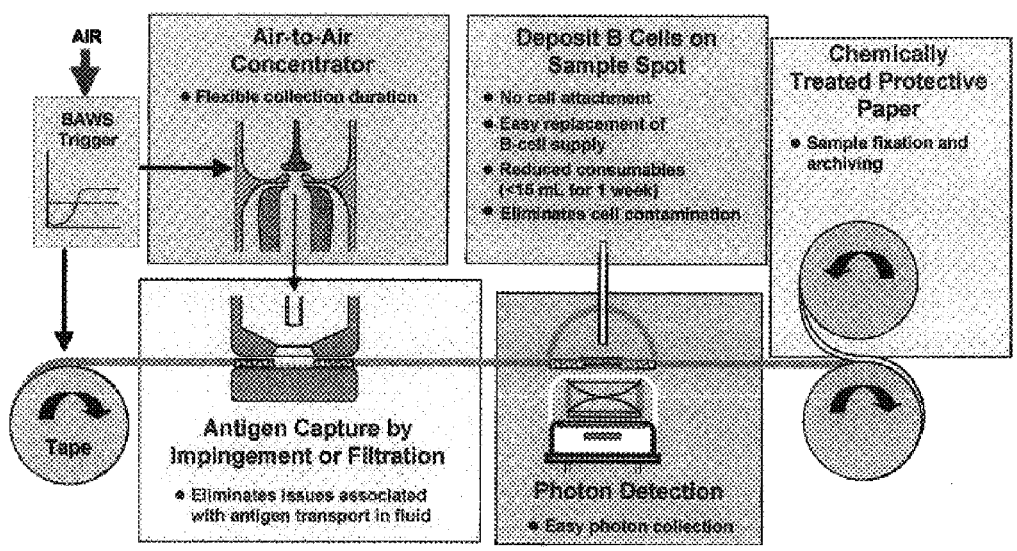
FIG. 13 is a schematic illustrating an air impactor/optoelectronic sensor.
Figure 14:
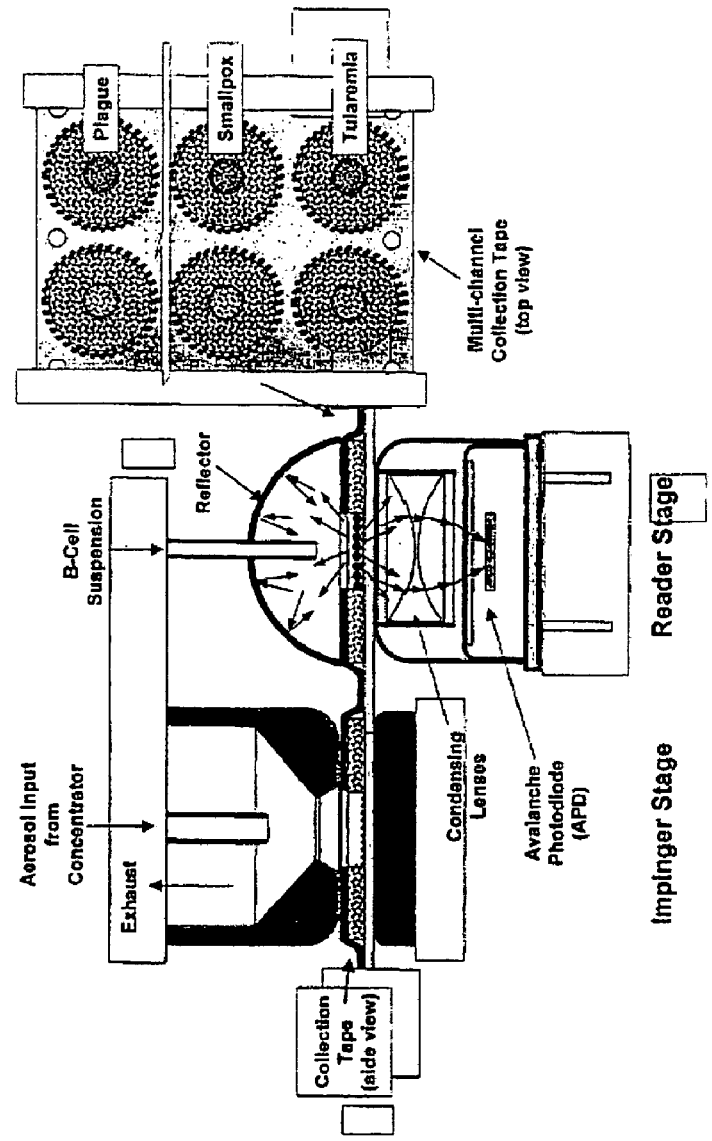
FIG. 14 is a schematic illustrating an optoelectronic sensor.

FIGS. 13–14 describe a different embodiment of the invention that does not require centrifugation. The schematic diagram of FIG. 13 shows the various components of this embodiment. A biological aerosol warning sensor (BAWS) detects the present of particles, e.g., within a pre-determined size range. An example of a BAWS is described in Primmerman, Lincoln Laboratory Journal 12:3–32, 2000. If particles meeting specifications are detected, BAWS triggers an air-to-air concentrator (specimen collector; as described in U.S. Pat. No. 5,932,795) that allows particles of a particular size range to be collected and deposited in a well (reaction chamber) on a portion of a specimen tape at a first station, which is shown in different views in FIG. 14. After candidate particles are deposited in the well, the tape advances to a second station under a reservoir of emitter cells and over a PMT. Emitter cells specific for a particular antigen on a target particles are deposited in the well, and the photon emission from the well monitored.

During the time that candidate particles are detected by BAWS, the candidate particles can be deposited on consecutive wells as the tape is advanced through the first station (FIG. 14). In the second station, a plurality of emitter cell reservoirs, each containing emitter cells having different target specificities, are mounted on a turret that rotates a particular reservoir into position to deposit different emitter cells into the well. In this manner, different targets within the candidate particles can be detected, as shown in the schematic top view of the wells in FIG. 14. Of course, if the different emitter cells emit at different wavelengths, it is possible to deposit the different emitter cells into a single well containing candidate particles, provided that the PMT below the second station can distinguish photons of different wavelengths.

FIG. 16 shows schematically yet another embodiment of a system of the invention. In this embodiment, air particles are deposited in each of six wells within a row of a two-dimensional array (e.g., a tape having 6 rows and hundreds of columns) at a first station. As the array is advanced by one row, positioning the row in a second station, different emitter cells are deposited into each well within the row, and emission from all six reactions is detected simultaneously by a row PMTs under the second station. To aid adhesion of particles to the wells on the tape, the wells can be coated with an adhesive or a liquid.

CELL ENGINEERING AND ASSAY METHOD EXAMPLES

A. Cell Engineering Methods:

M12g3R cells were maintained at 37° C. in a humidified atmosphere of 5% $CO_2$ in RPMI 1640 supplemented with 10% fetal bovine serum, 1-mM sodium pyruvate, 2-mM L-glutamine, 100-μM nonessential amino acids, 50-μM 2-mercaptoethanol, 50-μg/ml streptomycin, and 50-U/ml penicillin, 250 ng/ml amphotericin B (Life Technologies). Cells were transfected with pCMV.AEQ.IRES.NEO via electroporation (270 V, 950 μF) and selected in 1 mg/ml G418 for two weeks. G418-resistant clones were screened for response to anti-IgM. Those clones with the greatest increase in photon emission upon crosslinking of the surface IgM were used in subsequent transfections to generate B-cell lines specific for particular pathogens. Surface expression of antibodies with engineered specificity is accomplished by co-transfection (via electroporation) with expression vectors for light and heavy chains, as well as with one that encodes a gene conferring resistance to puromycin. Puromycin-resistant pools and clones were selected on the basis of their response to antigen. The light chain expression vector, VKExpress, contains the constant region for the human kappa gene downstream of a multiple cloning site (MCS), under control of the human elongation factor-1α (EF-1α) promoter. The heavy chain vector was generated by modifying pDisplay (Invitrogen), retaining the cytomegalovirus (CMV) promoter and leader sequence, but replacing the platelet-derived growth factor (PDGF) receptor transmembrane domain with the gene for the membrane-bound constant region of murine IgM and removing both tags on either side of the MCS. The appropriate restriction sites are added to the antibody variable regions using PCR and the sequence of all PCR products is confirmed before cloning into the expression construct. The variable regions used to produce the recombinant antibody were cloned either from cDNA or from hybridomas using Reverse-Transcription (RT) with random oligonucleotide primers and PCR. RNA was extracted with Trizol reagent (Life Technologies), according to the manufacturers recommendations, and first strand synthesis performed using the Retroscript kit (Ambion). PCR was accomplished using sets of primers designed to anneal to the leader sequences of either light or heavy chains [S. T. Jones and M. M. Bendig, *Bio/Technology* 9, 88 (1991)] at the 5' end, and the constant regions of murine Kappa or IgG2 at the 3' end.

B. Bioluminescent B-cell Response to FMDV:

The M12g3R B-cell line, stably transfected with the pCMV.AEQ.IRES.NEO plasmid and expression vectors for a recombinant antibody that recognizes the A12 strain of FMDV, was prepared for the luminesence assay as follows: Cells were thawed on Day 1. Preparation of the cells 24 hours post-thaw is critical for maximum activity and reliability. The freeze/thaw step increases the response of the B cells by as much as 100 fold. On Day 2, $10^6$ cells were incubated at room temperature for 2 hours in assay medium [$CO_2$—Independent medium, 10% FBS, 50-μg/ml streptomycin, and 50-U/mil penicillin, 250 ng/ml amphotericin B (Life Technologies)] with 50-μM coelenterazine (Molecular Probes, Eugene, Oreg.) covered with foil, washed twice, and resuspended in assay medium at a final concentration of $5\times10^5$ cells/ml. Cells were left rotating overnight at room temperature in 1.5 ml microcentrifuge tubes and assayed 15–20 hours later. For the assay, 25 μl of cells was mixed with antigen (5 μl of the wt A12pRMC35 strain at $1.4\times10^8$ pfu/ml, 10 μl of the A12 variant, B2PD.3, at $7.5\times10^7$ pfu/ml) and the response measured in a luminometer (Lumat LB 9507, Perkin Elmer).

C. Bioluminescent Assay with Bacteria and Large Viruses:

The sensor device and methods can be used for the rapid detection of bacterial, as well as viral pathogens. Cell lines were engineered to respond to the bacterium, *Francisella tularensis*, the etiological agent of tularemia. However, when assayed using the same protocol as with the FMD and VEE viruses, the signal is slow and almost indistinguishable from background, indicative of low interaction rates between the B cells and antigen (0s pre-spin/0s spin). Previous experiments performed with antigen-bead simulants have indicated that sensitivity and speed could be augmented by concentration of antigen and B cells (data not shown), so the luminometer was re-configured to include a centrifuge positioned above the photomultiplier tube (PMT). When the agent and cells are mixed together, then concentrated by centrifugation for 5 seconds, the signal is improved and the response faster (0s pre-spin/5s spin). Optimal results are observed when the slower-sedimenting *F. tularensis* is centrifuged prior to the addition of the cells (60s pre-spin/5s spin). This format ensures that a large number of cells come into physical contact with antigen within a short time frame, thereby providing a major improvement in sensitivity and speed. After additional optimization of the assay protocol, we can now detect as little as 60 colony-forming units (cfu) of *F. tularensis* in less than 3 minutes, including the time it takes to pre-spin the agent, but see no response to inactivated *Yersinia pestis*, the bacterium that causes the plague. This limit of detection has been confirmed with two other sources of inactivated *F. tularensis*, and one different strain (data not shown). Furthermore, the sensor device exhibits a wide range of sensitivity, detecting concentrations ranging over 7 orders of magnitude.

B-cells were prepared as described above. 50 µl containing the indicated amounts of *Y. pestis* or *F. tularensis* were centrifuged for 60 s at 6500×g, then 20 µl of cells were added and spun an additional 5 s in the centrifuge luminometer. Photons were detected with a Hamamatsu HC-125 photomultiplier tube and the signal monitored with a Stanford Research Systems SR400 Gated Photon Counter.

OTHER EMBODIMENTS

It is to be understood that while the invention has been described in conjunction with the detailed description thereof, the foregoing description is intended to illustrate and not limit the scope of the invention, which is defined by the appended claims. Other aspects, advantages, and modifications are within the scope of this invention.

What is claimed is:

1. An optoelectronic system for detecting a target particle, the system comprising
    a first reaction chamber;
    a specimen collector for collecting candidate particles present in a medium, the collector configured to deposit the candidate particles in the first reaction chamber;
    a first reservoir containing first emitter cells, each of the first emitter cells having first receptors which are expressed on the surface of each first emitter cell and are specific for a first target particle to be detected, wherein each first emitter cell further having a first emitter molecule which, in response to the binding of the first target particle to the first receptors, emits a first photon, wherein the first reservoir is configured to deposit at least a portion of the first cells into the first reaction chamber;
    a localization mechanism to facilitate contact between the first emitter cells and said candidate particles, said mechanism coupled to the reaction chamber;
    a control mechanism coupled to said reaction chamber for depositing said candidate particles and at least a portion of the first emitter cells in a sequential order;
    a particle detector coupled to said control mechanism, said particle detector arranged to detect the size of said candidate particles in the collector, wherein if the particle size detector detects the candidate particles having a size greater than a reference size, then the control mechanism is configured to deposit said at least portion of the first emitter cells first, and deposit the candidate particles thereafter and if the particle size detector detects the candidate particles having a size less than said reference size, then the control mechanism is configured to deposit the candidate particles first, and deposit said at least a portion of the first emitter cells thereafter; and
    an optical detector arranged for receiving the photon emitted from the first emitter cell.

2. The optoelectronic system of claim 1, a wherein the control mechanism is a movable stage, wherein at a first station, the stage positions the first reaction chamber in a first conflauration that allows the specimen collector to deposit the candidate particles in the first reaction chamber, and wherein at a second station, the stage positions the first reaction chamber in a second configuration that allows the first reservoir to deposit said at least a portion of the first emitter cells in the first reaction chamber.

3. The optoelectronic system of claim 2, wherein the sequential order is deposition of said at least a portion of the first emitter cells first, and deposition of the candidate particles thereafter.

4. The optoelectronic system of claim 2, wherein the sequential order is deposition of the candidate particles first, and deposition of said at least a portion of the first emitter cells thereafter.

5. The optoelectronic system of claim 1, wherein the localization mechanism facilitates said contact between the first emitter cells and the candidate particles by localizing the first emitter cells or the candidate particles to a small volume within the reaction chamber.

6. The optoelectronic system of claim 5, wherein the localization mechanism facilitates said contact between the first emitter cells and the candidate particles by localizing the first emitter cells and the candidate particles to a small volume within the reaction chamber.

7. The optoelectronic system of claim 6, wherein the small volume is a layer.

8. The optoelectronic system of claim 6, wherein the localization mechanism is selected from the group consisting of a centrifuge, an air impactor, a surface capture device, an affinity capture device, flow cells, an electric field, an electrophoretic trap, an isoelectric focusing device, a traveling-wave dielectrophoretic device, magnetically tagged particles, a wick, a filter and a membrane.

9. The optoelectronic system of claim 1, wherein the optical detector is selected from the group consisting of a charge-coupled device, avalanche photodiode, complimentary metal oxide semiconductor (CMOS) imager, photomultiplier and photomultiplier array tube.

10. The optoelectronic system of claim 1, wherein the medium is selected from the group consisting of a gas and a liquid.

11. The optoelectronic system of claim 1, wherein the first emitter cells are B cells.

12. The optoelectronic system of claim 11, wherein the B cells contain an artificial expression plasmid that encodes the first receptors.

13. The optoelectronic system of claim 1, wherein the first receptors are single chain antibodies.

14. The optoelectronic system of claim 1, wherein the candidate particles are selected from the group consisting of a virus, bacterium, protein, nucleic acid, fungus, protozoa, multicellular parasite, and prion.

15. The optoelectronic system of claim 1, wherein a sample is simultaneously analyzed for a plurality of target particles.

16. The optoelectronic system of claim 1, wherein a plurality of samples are simultaneously analyzed for a target particle.

17. The optoelectronic system of claim 1, wherein a plurality of samples are simultaneously analyzed for a plurality of target particles.

18. The optoelectronic system of claim 17, wherein the first reservoir further contains second cells, each of the second cells having second receptors which are expressed on the surface of each of the second cells and are specific for a second target particle to be detected, wherein each second cell further having a second emitter molecule which, in response to the binding of the second target particle to the second receptors, emits a second photon, wherein the first reservoir is configured to deposit at least a portion of the second cells into the first reaction chamber, and wherein the second photon has a wavelength different from the first photon.

19. The optoelectronic system of claim 1, further comprising an air sampling device.

* * * * *